US008137697B1

(12) United States Patent
Sung et al.

(10) Patent No.: US 8,137,697 B1

(45) **Date of Patent: *Mar. 20, 2012**

(54) NANOPARTICLES FOR PROTEIN/PEPTIDE DELIVERY AND DELIVERY MEANS THEREOF

(75) Inventors: Hsing-Wen Sung, HsinChu (TW); Mei-Chin Chen, Taipei County (TW); Po-Wei Lee, Jhonghe (TW); Hosheng Tu, Newport Beach, CA (US)

(73) Assignees: GP Medical, Inc., Newport Beach, CA (US); National Tsing Hua University, Hsinchu (TW)

( * ) Notice: Subject to any disclaimer, the term of this patent is extended or adjusted under 35 U.S.C. 154(b) by 127 days.

This patent is subject to a terminal disclaimer.

(21) Appl. No.: 12/381,684

(22) Filed: Mar. 13, 2009

Related U.S. Application Data

(63) Continuation-in-part of application No. 11/974,836, filed on Oct. 16, 2007, now Pat. No. 7,901,711, which is a continuation-in-part of application No. 11/405,066, filed on Apr. 17, 2006, now Pat. No. 7,449,200, which is a continuation-in-part of application No. 11/029,082, filed on Jan. 4, 2005, now Pat. No. 7,265,090, which is a continuation-in-part of application No. 10/958,864, filed on Oct. 5, 2004, now Pat. No. 7,348,026.

(51) Int. Cl.
*A61K 9/14* (2006.01)
*A61K 38/00* (2006.01)
*A61K 38/28* (2006.01)

(52) U.S. Cl. ........................................ 424/489; 514/5.9

(58) Field of Classification Search ........................ None
See application file for complete search history.

(56) References Cited

U.S. PATENT DOCUMENTS

| | | | | |
|---|---|---|---|---|
| 5,899,880 | A | 5/1999 | Bellhouse et al. | |
| 6,194,389 | B1 | 2/2001 | Johnston et al. | |
| 6,475,995 | B1 * | 11/2002 | Roy et al. | 514/44 R |
| 7,265,090 | B2 * | 9/2007 | Sung et al. | 514/1.2 |
| 7,449,200 | B2 * | 11/2008 | Sung et al. | 424/489 |
| 7,455,830 | B2 * | 11/2008 | Sung et al. | 424/1.69 |
| 7,541,046 | B1 * | 6/2009 | Sung et al. | 424/408 |
| 7,879,313 | B1 * | 2/2011 | Sung et al. | 424/1.69 |
| 7,901,666 | B1 * | 3/2011 | Sung et al. | 424/1.69 |
| 7,910,086 | B1 * | 3/2011 | Sung et al. | 424/1.69 |
| 7,985,426 | B1 * | 7/2011 | Sung et al. | 424/489 |
| 7,988,949 | B2 * | 8/2011 | Sung et al. | 424/1.69 |
| 7,993,624 | B2 * | 8/2011 | Sung et al. | 424/1.69 |
| 7,993,625 | B1 * | 8/2011 | Sung et al. | 424/1.69 |
| 7,998,459 | B1 * | 8/2011 | Sung et al. | 424/1.69 |
| 8,007,768 | B1 * | 8/2011 | Sung et al. | 424/1.69 |
| 8,038,985 | B1 * | 10/2011 | Sung et al. | 424/1.73 |
| 8,048,404 | B1 * | 11/2011 | Sung et al. | 424/1.69 |
| 2011/0104069 | A1 * | 5/2011 | Xu et al. | 424/9.6 |

OTHER PUBLICATIONS

Nie et al. Synthesis and characterization of monodisperse chitosan nanoparticles with embedded quantum dots. Nanotechnology, 2006, vol. 17, pp. 140-144.*

Howard et al. RNA Interference in Vitro and in Vivo Using a Chitosan/siRNA Nanoparticle System. Molecular Therapy, Oct. 2006, vol. 14, Nol. 4, pp. 476-484.*

Lin et al. Preparation of Nanoparticles Composed of Chitosan/Poly-gamma-glutamic Acid and Evaluation of Their Permeability through Caco-2 Cells. Biomacromolecules, 2005, vol. 6, pp. 1104-1112.*

Lin YH et al., "Novel nanoparticles for oral insulin delivery via the paracellular pathway" Nanotechnology 2007;18:1-11.

Ogura M et al., "In vivo targeted gene transfer in skin by the use of laser-induced stress waves" Lasers Surg. Med. 2004;34:242-248.

Douglas KL et al., "Effects of alginate inclusion on the vector properties of chitosan-based nanoparticles" J. Control. Release 2006;115:354-361.

Soppimath KS et al., "Biodegradable polymeric nanoparticles as drug delivery devices" J. Control. Release 2001;70:1-20.

Mikszta JA et al., "Improved genetic immunization via micromechanical disruption of skin-barrier function and targeted epidermal delivery" Nature Medicine 2002;8:415-419.

Roy K et al., "Oral gene delivery with chitosan-DNA nanoparticles generates immunologic protection in a murine model of peanut allergy" Nature Medicine 1999;5:387-391.

Qaqish RB et al., "Synthesis of a fluoroscent chitosan derivative and its application for the study of chitosan-mucin interactions" Carbohy. Polym. 1999;38:99-107.

Corsi K et al., Mesenchymal stem cells, MG63 and HEK293 transfection using chitosan-DNA nanoparticles Biomaterials 2003;24:1255-1264.

Liu W et al., "An investigation of the physicochemical properties of chitosan/DNA polyelectrolyte complexes" Biomaterials 2005;26"2705-2711.

Ye H et al., "Poly(r,L-glutamic acid)-cisplatin conjugate effectively inhibits human breast tumor xenografted in nude mice" Biomaterials 2006;27:5958-5965.

Erbacher P et al., "Chitosan-based vector/DNA complexes for gene delivery: biophysical characteristics and transfection ability" Pharma. Res. 1998;15:1332-1339.

Mao HQ et al., "Chitosan-DNA nanoparticles as gene carriers: synthesis, characterization and transfection efficiency" J. Control. Release 2001;70:399-421.

Cui Z et al., "Chitosan-based nanoparticles for topical genetic immunization" J Control. Release 2001;75:409-419.

Hsu WL et al., "Thermally-induced order-order transition of DNA-cationic surfactant complexes" Langmuir 2006;22:7521-7527.

Dang JM et al., "Natural polymers for gene delivery and tissue engineering" Adv. Drug Deliv. Rev. 2006;58:487-499.

(Continued)

*Primary Examiner* — Marcela M Cordero Garcia

(57) ABSTRACT

The invention discloses the biodegradable nanoparticle for use in nanoparticle projectile bombardment as a carrier for administering nucleic acid, DNA, RNA or siRNAs transdermally to an animal subject. The nanoparticles are composed of positively charged chitosan substrate and the nucleic acid encapsulated within the nanoparticles or electrostatically loaded on the exterior surface of the nanoparticles.

19 Claims, 14 Drawing Sheets

OTHER PUBLICATIONS

Kendall M et al., "Intradermal ballistic delivery of micro-particles into excised human skin for pharmaceutical applications" J Biomechanics 2004;37:1733-1741.

Pack DW et al., "Design and development of polymer for gene delivery" Nature Reviews 2005;4:581-593.

Pertmer TM et al., "Gene gun-based nucleic acid immunization:elicitation of humoral and cytotoxic T lymphocyte responses following epodermal delivery of nanogram quantities of DNA" Vaccine 1995;13:1427-1430.

* cited by examiner

NANOPARTICLES FOR PROTEIN/PEPTIDE DELIVERY AND DELIVERY MEANS THEREOF

CROSS-REFERENCE TO RELATED APPLICATIONS

This application is a continuation-in-part application of U.S. patent application Ser. No. 11/974,836, filed Oct. 16, 2007, now U.S. Pat. No. 7,901,711, which is a continuation-in-part application of U.S. patent application Ser. No. 11/405,066, filed Apr. 17, 2006, now U.S. Pat. No. 7,449,200, which is a continuation-in-part application of U.S. patent application Ser. No. 11/029,082, filed Jan. 4, 2005, now U.S. Pat. No. 7,265,090, which is a continuation-in-part application of U.S. patent application Ser. No. 10/958,864, filed Oct. 5, 2004, now U.S. Pat. No. 7,348,026, the entire contents of which are incorporated herein by reference.

FIELD OF THE INVENTION

The present invention is related to pharmaceutical formulation and medical uses of nanoparticles encapsulating bioactive agents and the delivery means to an animal subject via transdermal routes.

BACKGROUND OF THE INVENTION

Production of pharmaceutically active peptides and proteins in large quantities has become feasible (Biomacromolecules 2004; 5:1917-1925). The oral route is considered the most convenient way of drug administrations for patients. Nevertheless, the intestinal epithelium is a major barrier to the absorption of hydrophilic drugs such as peptides and proteins (J. Control. Release 1996; 39:131-138). This is because hydrophilic drugs cannot easily diffuse across the cells through the lipid-bilayer cell membranes. Furthermore, following the oral drug delivery route, protein drugs are readily degraded by the low pH of gastric medium in the stomach.

Polymeric nanoparticles have been widely investigated as carriers for drug delivery (Biomaterials 2002; 23:3193-3201). Much attention has been given to the nanoparticles made of synthetic biodegradable polymers such as poly-ϵ-caprolactone and polylactide due to their good biocompatibility (J. Drug Delivery 2000; 7:215-232; Eur. J. Pharm. Biopharm. 1995; 41:19-25). However, these nanoparticles are not ideal carriers for hydrophilic drugs because of their hydrophobic property. Some aspects of the invention relate to a novel nanoparticle system, composed of hydrophilic chitosan and poly(glutamic acid) hydrogels that is prepared by a simple ionic-gelation method. This technique is promising as the nanoparticles are prepared under mild conditions without using harmful solvents or elevated temperatures. It is known that organic solvents may cause degradation of peptide or protein drugs that are unstable and sensitive to their environments (J. Control. Release 2001; 73:279-291).

Chitosan (CS), a cationic polysaccharide, is generally derived from chitin by alkaline deacetylation (J. Control. Release 2004; 96:285-300). It was reported from literature that CS is non-toxic and soft-tissue compatible (Biomacromolecules 2004; 5:1917-1925; Biomacromolecules 2004; 5:828-833). Most commercially available CSs have quite large molecular weight (MW) and need to be dissolved in an acetic acid solution at a pH value of approximately 4.0 or lower that is sometimes impractical. However, there are potential applications of CS in which a low MW would be essential. Given a low MW, the polycationic characteristic of CS can be used together with a good solubility at a pH value close to physiological ranges (Eur. J. Pharm. Biopharm. 2004; 57:101-105). Loading of peptide or protein drugs at physiological pH ranges would preserve their bioactivity. On this basis, a low-MW CS, obtained by depolymerizing a commercially available CS using cellulase, is disclosed herein in preparing nanoparticles of the present invention.

The γ-PGA, an anionic peptide, is a natural compound produced as capsular substance or as slime by members of the genus *Bacillus* (Crit. Rev. Biotechnol. 2001; 21:219-232). γ-PGA is unique in that it is composed of naturally occurring L-glutamic acid linked together through amide bonds. It was reported from literature that this naturally occurring γ-PGA is a water-soluble, biodegradable, and non-toxic polymer. A related, but structurally different polymer, [poly(α-glutamic acid), α-PGA] has been used for drug delivery (Adv. Drug Deliver. Rev. 2002; 54:695-713; Cancer Res. 1998; 58:2404-2409). α-PGA is usually synthesized from poly(γ-benzyl-L-glutamate) by removing the benzyl protecting group with the use of hydrogen bromide. Hashida et al. used α-PGA as a polymeric backbone and galactose moiety as a ligand to target hepatocytes (J. Control. Release 1999; 62:253-262). Their in vivo results indicated that the galactosylated α-PGA had a remarkable targeting ability to hepatocytes and degradation of α-PGA was observed in the liver.

U.S. Pat. No. 6,194,389 issued on Feb. 27, 2001, entire contents of which are incorporated herein by reference, discloses a method of administering a protein or peptide in a vertebrate subject by in situ microprojectile bombardment, comprising the steps of providing microprojectiles, the microprojectiles carrying polynucleic acid sequences; and accelerating the microprojectiles at the cells, with the microprojectiles contacting the cells at a speed sufficient to penetrate the cells and deposit the polynucleic acid sequences therein.

Skin is an attractive target for delivery of genetic therapies and vaccines. Gene guns have been reportedly used for delivery of DNA-coated gold particles through the stratum corneum to the epidermis by pressurized helium. The coated DNA can be bombarded directly into the cytoplasm and nuclei of cells facilitating expression of the encoded protein. However, the DNA coated on the exterior surfaces of gold particles is liable to be digested by DNase and lacks the ability of controlled release. Further disadvantage of conventional gene-gun bombardments is that the non-biodegradable gold particles may cause adverse side effects when over-accumulated. In view of the foregoing, an object of this invention is to provide new uses of nanoparticles encapsulated with nucleic acid (for example, plasmid DNA (pDNA), RNA or siRNA) as a potential delivery vehicle to genetic immunization by nanoparticle projectile bombardment.

SUMMARY OF THE INVENTION

Some aspects of the invention provide a novel nanoparticle system for topical transcutaneous or transdermal delivery or targeted epidermal delivery of the biodegradable nanoparticles that encapsulate at least one bioactive agent of protein/peptides, nucleic acid (for example pDNA, RNA, or siRNA) via nanoparticle projectile bombardment or other transcutaneous/transdermal means. In one embodiment, the system includes micro-sized particles or nano-sized particles. One aspect of the invention provides a method of preparing the nanoparticles using a simple and mild ionic-gelation method upon addition of bioactive agent containing polyanionic solution into chitosan solution. A particular aspect of the invention provides a method of preparing the nanoparticles by adding a mixture of poly-γ-glutamic acid (γ-PGA) and bioactive agent solution into chitosan (CS) solution made of regular molecular weight chitosan or low molecular weight chitosan. In one embodiment, the molecular weight of a low-MW CS of the present invention is about 80 kDa or less, preferably at about 40 kDa, adapted for adequate solubility at a pH that maintains the bioactivity of protein and peptide drugs. It was suggested that a chitosan substrate with about 30-50 kDa molecular weight is kidney inert. In one embodiment, the chitosan raw material is a low molecular weight CS that is readily dissolvable in a solution with a pH range of about 4.0 to 6.5, preferably about 6.0 to 6.5.

In one embodiment, the chitosan dominates on surface of the nanoparticles as shell substrate and the negatively charged component (for example, γ-PGA, α-PGA, water-soluble salts of PGA, metal salts of PGA, heparin, heparin analogs, low molecular weight heparin, glycosaminoglycans, or alginate) as a component of the core substrate. In another embodiment, a substantial portion of the surface of the nanoparticles is characterized with a positive surface charge. In a further embodiment, the nanoparticles of the present invention comprise at least one positively charged shell substrate and at least one negatively charged core substrate, wherein the core substrate is selected from the group consisting of heparin, heparin analogs, low molecular weight heparin, glycosaminoglycans, and alginate. In one embodiment, at least one bioactive agent or protein/peptide is conjugated with the core substrate.

Some aspects of the invention provide a transcutaneous, transdermal, or targeted epidermal delivery of bioactive nanoparticles loaded with at least one bioactive agent, wherein the nanoparticles comprise a shell portion that is dominated by positively charged chitosan, a core portion that contains negatively charged substrate, wherein said negatively charged substrate is at least partially neutralized with a portion of said positively charged chitosan. In one embodiment, the chitosan is N-trimethyl chitosan or chitosan derivatives.

Some aspects of the invention provide a method of using nanoparticle projectile bombardment as a means for administering proteins/peptides or virus encapsulated in non-metallic nanoparticles to an animal subject. In one embodiment, the non-metallic nanoparticles are biodegradable. In one preferred embodiment, the biodegradable nanoparticles provide sustained release of encapsulated proteins or peptides. In another embodiment, the nanoparticles are crosslinked with a crosslinking agent or with light, such as ultraviolet irradiation. In one embodiment, the degree of crosslinking is less than 50%. In another embodiment, the degree of crosslinking is in a range between 1% and 20% of the total available crosslink sites.

In a further embodiment, the nanoparticles of the present invention have a mean particle size between about 50 and 500 nanometers, preferably between about 100 and 300 nanometers, and most preferably between about 150 and 250 nanometers.

In some embodiments, the nanoparticles are loaded with a therapeutically effective amount of at least one bioactive agent, wherein the bioactive agent is selected from the group consisting of proteins, peptides, nucleosides, nucleotides, antiviral agents, antineoplastic agents, antibiotics, anti-inflammatory drugs, and combinations thereof. Further, the bioactive agent may be selected from the group consisting of calcitonin, cyclosporin, insulin, insulin analogs, oxytocin, tyrosine, enkephalin, tyrotropin releasing hormone, follicle stimulating hormone, luteinizing hormone, vasopressin and vasopressin analogs, catalase, superoxide dismutase, interleukin-2, interleukin-11, interferon, colony stimulating factor, tumor necrosis factors, tumor necrosis factor inhibitors, melanocyte-stimulating hormone, and the like. In one preferred embodiment, the bioactive agent is an Alzheimer antagonist, calcitonin, vancomycin, chondroitin sulfate, hyaluronic acid, growth factor and protein drugs with pharmaceutically effective amount to the animal subject.

Some aspects of the invention provide nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle, wherein the at least one bioactive agent is an antagonist for Alzheimer's disease or is for treating Alzheimer's disease selected from the group consisting of memantine hydrochloride, donepezil hydrochloride, rivastigmine tartrate, galantamine hydrochloride, tacrine hydrochloride, and the like. In a further embodiment, the at least one bioactive agent is insulin or insulin analog, wherein the molecular formula of the insulin/insulin analog is selected from the group consisting of $C_{254}H_{377}N_{65}O_{75}S_6$, $C_{257}H_{383}N_{65}O_{77}S_6$, $C_{256}H_{381}N_{65}O_{79}S_6$, $C_{267}H_{404}N_{72}O_{78}S_6$, and the like.

Some aspects of the invention provide a method of administering a bioactive agent in an animal subject by in situ nano-projectile bombardment, comprising: selecting a target skin tissue of the animal subject, wherein the target skin tissue is selected from the group consisting of epidermis tissue, dermis tissue, and hypodermis tissue; providing nano-projectiles, wherein the bioactive agent is encapsulated in the nano-projectiles, each nano-projectile being in a nanoparticle form; and accelerating the nano-projectiles toward the animal subject so that the nano-projectiles contact the animal's epidermis at a speed sufficient to penetrate the epidermis and lodge in the target skin tissue, wherein the accelerating step is carried out by a nano-projectile bombardment gun. In one embodiment, the instant invention discloses a nano-/microparticle system used in the method for administering nucleic acid (for example, DNA, RNA, short interfering, double-stranded, micro or short hairpin RNA) by in situ projectile bombardment means into the tissue or tissue cells.

This invention provides a nanoparticle system comprising compounds, compositions, and methods useful for modulating the expression of genes, such as those genes loaded with angiogenesis and proliferation, using short interfering RNA molecules. Some aspects of the invention further provide a nanoparticle system that comprises compounds, compositions, and methods useful for modulating the expression and activity of vascular endothelial growth factor (VEGF) and/or vascular endothelial growth factor receptor (e.g., VEGFr1, VEGFr2, VEGFr3) genes, or genes involved in VEGF and/or VEGFr pathways of gene expression and/or VEGF activity by RNA interference (RNAi) using small nucleic acid molecules.

Some aspects of the invention provide a nanoparticle system used in the method of administering the siNA in a living subject by in situ nano-projectile bombardment or percutaneous injection, the nanoparticle system comprising chemically synthesized double stranded short interfering nucleic acid (siNA) molecule that directs cleavage of a vascular endothelial growth factor receptor 1 (VEGEr1) RNA via RNA interference (RNAi).

Some aspects of the invention provide a pharmaceutical composition of nanoparticles for transdermally lodging in a target tissue of an animal or living subject, each nanoparticle comprising a first component of a positively charged chitosan, a second component of negatively charged substrate that complexes with the first positively charged component, and at least one bioactive agent encapsulated within the nanoparticles. In one embodiment, the nanoparticles are biodegradable. In another embodiment, the nanoparticle is about 50 nm to 500 nm in size.

One aspect of the invention provides a pharmaceutical composition of nanoparticles for transdermally lodging in a target tissue of an animal subject, each nanoparticle comprising a first component of a positively charged chitosan, a second component of negatively charged substrate that complexes with the first positively charged component, wherein the second component comprises a material selected from the group consisting of γ-PGA, α-PGA, PGA derivatives, glycosaminoglycans, and alginate. In one embodiment, the second component comprises heparin and small molecular weight heparin.

One aspect of the invention provides a pharmaceutical composition of nanoparticles for transdermally lodging in a target tissue of an animal subject, wherein the bioactive agent encapsulated within the nanoparticles is a protein, a peptide, a plasmid protein, a ribonucleic acid, a deoxyribonucleic acid, or a small interfering ribonucleic acid.

One aspect of the invention provides a pharmaceutical composition of nanoparticles for transdermally lodging in a target tissue of an animal subject, wherein the bioactive agent encapsulated within the nanoparticles comprises a growth factor.

One aspect of the invention provides a pharmaceutical composition of nanoparticles for transdermally lodging in a target tissue of an animal subject, wherein the nanoparticle is mixed with trehalose or hexan-1,2,3,4,5,6-hexyl in a freeze-drying process.

One aspect of the invention provides a pharmaceutical composition of nanoparticles for transdermally lodging in a target tissue of an animal subject, wherein the nanoparticle is crosslinked or partially crosslinked.

One aspect of the invention provides a pharmaceutical composition of nanoparticles for transdermally lodging in a target tissue of an animal subject, wherein the nanoparticle further comprises an adenovirus vector, the adenovirus vector comprising a small interfering ribonucleic acid.

One aspect of the invention provides a pharmaceutical composition of nanoparticles for transdermally lodging in a target tissue of an animal subject, wherein a surface of the nanoparticle is positively charged or chitosan-shelled. In an alternate embodiment, the surface of the nanoparticle is negatively charged.

Some aspects of the invention provide a process of administering nanoparticles having the pharmaceutical composition of the present invention into a living subject, wherein the process comprises a transdermal step so that the nanoparticles lodge in the target tissue of the living subject. In a preferred embodiment, the transdermal step of the process comprises an in situ nano-projectile bombardment, the bombardment comprising: (a) providing the nanoparticles as nano-projectiles; (b) loading the nano-projectiles in a nano-projectile pressurized gun; and (c) accelerating the nano-projectiles at a target skin of the living subject so that the nano-projectiles contact its epidermis at a speed sufficient to penetrate the epidermis and lodge in the target tissue.

One aspect of the invention provides an in situ nano-projectile bombardment for lodging the nanoparticles transdermally, wherein the speed in the accelerating step is generated by a pressure source for firing the nano-projectile pressurized gun at a pressure between about 10 psi and about 200 psi, preferably between about 20 psi and about 90 psi, most preferably between about 20 psi and about 50 psi.

Some aspects of the invention provide multifunctional core-shelled nanoparticles, wherein their core-shelled structure has been verified via TEM. The core portion of the nanoparticles encapsulate at least one quantum dot (QD) by emulsion-solvent evaporation techniques. The nanoparticles exhibit a pH-responsive property due to the shelled amino groups of polyvinyl alcohol (PVA)-glycol chitosan (gCS) which could be loaded with nucleic acid (such as DNA, RNA) or can conjugate with ligands or antibodies for targeted drug/DNA delivery. In one embodiment, the core-shelled nanoparticles also enable as a delivery carrier for genetic immunization using an air injector (for example, a nanoparticle projectile bombardment element) and the Langerhans cells (LCs) migration could be tracked by this technique.

Some aspects of the invention provide a pharmaceutical composition of nanoparticles for transdermal nucleic acid delivery, the nanoparticles comprising a first component of a positively charged chitosan and the nucleic acid, wherein said nucleic acid is encapsulated within said nanoparticles or electrostatically loaded on an exterior surface of said nanoparticles, said nanoparticles having a mean particle size between about 50 and 500 nanometers. In one embodiment, the nanoparticles further comprise a second component of negatively charged substrate in a core portion of said nanoparticles, said second component being complexed with said first component, wherein said second component comprises a material selected from the group consisting of γ-PGA, α-PGA, PGA derivatives, glycosaminoglycans, heparin, and small molecular weight heparin. In one embodiment, the nucleic acid of the present invention comprises DNA, RNA, siRNA, and pDNA.

Some aspects of the invention provide a pharmaceutical composition of nanoparticles for transdermal nucleic acid delivery, the nanoparticles comprising a first component of a positively charged chitosan, the nucleic acid being encapsulated within said nanoparticles or electrostatically loaded on an exterior surface of said nanoparticles, and at least one quantum dot in a core portion. In one embodiment, the quantum dot is a CdSe/ZnS quantum dot.

Some aspects of the invention provide a pharmaceutical composition of nanoparticles for transdermal nucleic acid delivery, the nanoparticles comprising (a) a first component of a positively charged chitosan, (b) the nucleic acid being encapsulated within said nanoparticles or electrostatically loaded on an exterior surface of said nanoparticles, (c) at least one quantum dot in a core portion, and (d) PLGA substrate in the core portion, wherein said at least one quantum dot is dispersed within said PLGA substrate.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

DETAILED DESCRIPTION OF THE EXEMPLARY EMBODIMENTS

Figure 1:
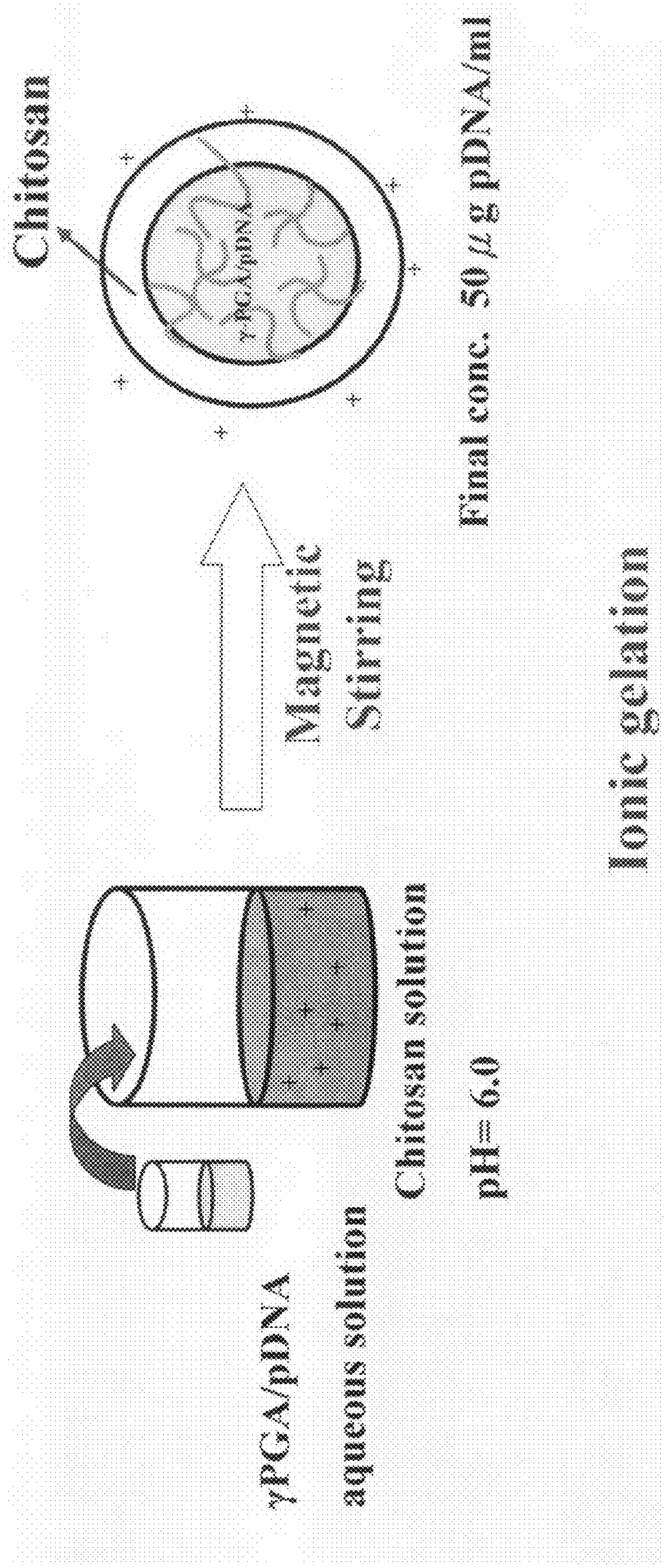
FIG. 1 shows a simple ionic gelation process for nanoparticles manufacturing.

The preferred embodiments of the present invention described below relate particularly to preparation of nanoparticles composed of chitosan/poly-glutamic acid/insulin or chitosan/poly-glutamic acid/pDNA for transcutaneous or transdermal delivery via nanoparticle projectile bombardment. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

The γ-PGA is a naturally occurring anionic homo-polyamide that is made of L-glutamic acid units connected by amide linkages between α-amino and γ-carboxylic acid groups (Crit. Rev. Biotechnol. 2001; 21:219-232). It is an exocellular polymer of certain *Bacillus* species that is produced within cells via the TCA cycle and is freely excreted into the fermentation broth. Its exact biological role is not fully understood, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been studied in the past few years.

EXAMPLE NO. 1

Materials and Methods of Nanoparticles Preparation

CS (MW ~$2.8\times10^5$) with a degree of deacetylation of approximately 85% was acquired from Challenge Bioproducts Co. (Taichung, Taiwan). Acetic acid, cellulase (1.92 units/mg), fluorescein isothiocyanate (FITC), phosphate buffered saline (PBS), periodic acid, sodium acetate, formaldehyde, bismuth subnitrate, and Hanks balanced salt solution (HBSS) were purchased from Sigma Chemical Co. (St. Louis, Mo.). Ethanol absolute anhydrous and potassium sodium tartrate were obtained from Merck (Darmstadt, Germany). Non-essential amino acid (NEAA) solution, fetal bovine serum (FBS), gentamicin and trypsin-EDTA were acquired from Gibco (Grand Island, N.Y.). Eagle's minimal essential medium (MEM) was purchased from Bio West (Nuaille, France). All other chemicals and reagents used were of analytical grade.

EXAMPLE NO. 2

Depolymerization of CS by Enzymatic Hydrolysis

Regular CS was treated with enzyme (cellulase) to produce low-MW CS according to a method described by Qin et al. with some modifications (Food Chem. 2004; 84:107-115). A solution of CS (20 g/l) was prepared by dissolving CS in 2% acetic acid. Care was taken to ensure total solubility of CS by filtration. Then, the CS solution was introduced into a vessel and adjusted to the desired pH 5.0 with 2N aqueous NaOH. Subsequently, cellulase (0.1 g) was added into the CS solution (100 ml) and continuously stirred at 37° C. for 12 hours. Afterward, the depolymerized CS was precipitated with aqueous NaOH at pH 7.0-7.2 and the precipitated CS was washed three times with deionized water to remove cellulose and any of very low molecular weight impurities. The resulting low-MW CS with a desired MW range was lyophilized in a freeze dryer (Eyela Co. Ltd, Tokyo, Japan).

The average molecular weight of the depolymerized CS was determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000—F, SFD, Torrance, Calif.). Polysaccharide standards (molecular weights range from 180 to 788,000, Polymer Laboratories, UK) were used to construct a calibration curve. The mobile phase contained 0.01M $NaH_2PO_4$ and 0.5M $NaNO_3$ and was brought to a pH of 2.0. The flow rate of mobile phase was 1.0 ml/min, and the columns and the RI detector cell were maintained at 30° C.

Factors limiting applications of most commercially available CSs are their high molecular weight and thus high viscosity and poor solubility at physiological pH ranges. Low-MW CS overcomes these limitations and hence finds much wider applications in diversified fields. It was suggested that low-MW CS be used as a parenteral drug carrier due to its lower antigen effect (Eur. J. Pharm. Biopharm. 2004; 57:101-105). Low-MW CS was used as a non-viral gene delivery system and showed promising results (Int. J. Pharm. 1999; 178:231-243). Other studies based on animal testing showed the possibilities of low-MW CS for treatment of type 2 diabetes and gastric ulcer (Biol. Pharm. Bull. 2002; 25:188-192). Several hydrolytic enzymes such as lysozyme, pectinase, cellulase, bromelain, hemicellulase, lipase, papain and the like can be used to depolymerize CS (Biochim. Biophys. Acta 1996; 1291:5-15; Biochem. Eng. J. 2001; 7:85-88; Carbohydr. Res. 1992; 237:325-332). It is known that cellulase catalyzes the cleavage of the glycosidic linkage in CS (Food Chem. 2004; 84:107-115). The low-MW CS used in the study was obtained by precipitating the depolymerized CS solution with aqueous NaOH at pH 7.0-7.2. The obtained low-MW CS had a MW of about 50 kDa. In a preferred embodiment, the low molecular weight chitosan has a molecular weight of less than about 40 kDa, but above 10 kDa. Other forms of chitosan may also be applicable, including chitin, chitosan oligosaccharides, and derivatives thereof.

It was observed that the low-MW CS can be readily dissolved in an aqueous solution at pH 6.0, while the standard-MW CS before depolymerization needs to be dissolved in an acetic acid solution with a pH value about 4.0. Additionally, it was found that with the low-MW CS, the prepared nanoparticles had a significantly smaller size with a narrower distribution than their counterparts prepared with the high-MW (also known as standard-MW) CS before depolymerization, due to its lower viscosity. As an example, upon adding a 0.10% γ-PGA aqueous solution into a 0.20% high-MW CS solution (viscosity 5.73±0.08 cp, measured by a viscometer), the mean particle size of the prepared nanoparticles was 878.3±28.4 nm with a polydispersity index of 1.0, whereas adding a 0.10% γ-PGA aqueous solution into the low-MW CS solution (viscosity 1.29±0.02 cp) formed nanoparticles with a mean particle size of 218.1±4.1 nm with a polydispersity index of 0.3 (n=5).

EXAMPLE NO. 3

Production and Purification of γ-PGA

The γ-PGA was produced by *Bacillus licheniformis* (ATCC 9945, Bioresources Collection and Research Center, Hsinchu, Taiwan) as per a method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (ingredients comprising L-glutamic acid, 20.0 g/l; citric acid, 12.0 g/l; glycerol, 80.0 g/l; $NH_4Cl$, 7.0 g/l; $K_2HPO_4$, 0.5 g/l; $MgSO_4.7H_2O$, 0.5 g/l; $FeCl_3.6H_2O$, 0.04 g/1; $CaCl_2.2H_2O$, 0.15 g/l; $MnSO_4.H_2O$, 0.104 g/l, pH 6.5) agar plates at 37° C. several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-l jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and/or 2M HCl. The dissolved oxygen concentration was initially controlled at 40% of air saturation by supplying air and by controlling the agitation speed up to 1000 rpm.

After 40 hours, cells were separated from the culture broth by centrifugation for 20 minutes at 12,000×g at 4° C. The supernatant containing γ-PGA was poured into 4 volumes of methanol and left overnight with gentle stirring. The resulting precipitate containing crude γ-PGA was collected by centrifugation for 40 minutes at 12,000×g at 4° C. and then was dissolved in deionized water to remove insoluble impurities by centrifugation for 20 minutes at 24,000×g at 4° C. The aqueous γ-PGA solution was desalted by dialysis (MWCO: 100,000, Spectrum Laboratories, Inc., Laguna Hills, Calif.) against distilled water for 12 hours with water exchanges several times, and finally was lyophilized to obtain pure γ-PGA.

The purified γ-PGA was verified by the proton nuclear magnetic resonance ($^1H$-NMR) and the FT-IR analyses. Analysis of $^1H$-NMR was conducted on an NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned from 400-4000 $cm^{-1}$. The average molecular weight of the purified γ-PGA was determined by the same GPC system as described before. Polyethylene glycol (molecular weights of 106-22,000) and polyethylene oxide (molecular weights of 20,000-1,000,000, PL Laboratories) standards were used to construct a calibration curve. The mobile phase contained 0.01M $NaH_2PO_4$ and 0.2M $NaNO_3$ and was brought to a pH of 7.0.

The purified γ-PGA obtained from fermentation was analyzed by GPC, $^1H$-NMR, and FT-IR. The purified γ-PGA had a MW of about 160 kDa. The fermented product after purification showed no detected macromolecular impurities by the $^1H$-NMR analysis, suggesting that the obtained white power of γ-PGA is highly pure. The applicable γ-PGA for nanoparticles of the present invention is between about 10 kDa and 100 kDa, preferably between about 20 kDa and 60 kDa.

EXAMPLE NO. 4

Preparation of the CS-γ-PGA Nanoparticles

Nanoparticles were obtained upon addition of γ-PGA aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at varying concentrations (0.01%, 0.05%, 0.10%, 0.15%, or 0.20% by w/v) under magnetic stirring at room temperature. Nanoparticles were collected by ultracentrifugation at 38,000 rpm for 1 hour. Supernatants were discarded and nanoparticles were resuspended in deionized water for further studies. FT-IR was used to analyze peak variations of amino groups of low-MW CS and carboxylic acid salts of γ-PGA in the CS-γ-PGA nanoparticles.

As stated, nanoparticles were obtained instantaneously upon addition of a γ-PGA aqueous solution (pH 7.4) into a low-MW CS aqueous solution (about pH 6.0) under magnetic stirring at room temperature. FIG. 1 shows a simple ionic gelation process for nanoparticles manufacturing. The electrostatic interaction between the two polyelectrolytes (γ-PGA and CS) instantaneously induced the formation of long hydrophobic segments (or at least segments with a high density of neutral ion-pairs), and thus resulted in highly neutralized complexes that segregated into colloidal nanoparticles.

EXAMPLE NO. 5

Characterization of the CS-γ-PGA Nanoparticles

Morphological examination of the CS-γ-PGA nanoparticles was performed by TEM (transmission electron microscopy) and/or AFM (atomic force microscopy). The TEM sample was prepared by placing a drop of the nanoparticle solution onto a 400 mesh copper grid coated with carbon. About 2 minutes after deposition, the grid was tapped with a filter paper to remove surface water and thereafter, positively stained by using an alkaline bismuth solution (Microbiol. Immunol. 1986; 30:1207-1211). The AFM sample was prepared by casting a drop of the nanoparticle solution on a slide glass and then dried in vacuum. The size distribution and zeta potential of the prepared nanoparticles were measured using a Zetasizer (3000HS, Malvern Instruments Ltd., Worcestershire, UK).

During storage, aggregation of nanoparticles may occur and thus leads to losing their structural integrity or forming precipitation of nanoparticles (Eur. J. Pharm. Sci. 1999; 8:99-107). Therefore, the stability of nanoparticles during storage must be evaluated. In the stability study, the prepared nanoparticles suspended in deionized water (1 mg/ml) were stored at 4° C. and their particle sizes and zeta potential values were monitored by the same Zetasizer as mentioned earlier during storage.

In the preparation of nanoparticles, samples were visually analyzed and three distinct solution systems were identified: clear solution, opalescent suspension, and solution with precipitation of aggregates. Examined by the Zetasizer, nanoparticles were found in the clear solution and the opalescent suspension rather than in the solution with precipitation of aggregates.

The particle sizes and the zeta potential values of CS-γ-PGA nanoparticles were determined and the results are shown in Tables 1a and 1b. It was found that the particle size and the zeta potential value of the prepared nanoparticles were mainly determined by the relative amount of the local concentration of γ-PGA in the added solution to the surrounding concentration of CS in the sink solution. At a fixed concentration of CS, an increase in the γ-PGA concentration allowed γ-PGA molecules interacting with more CS molecules, and thus formed a lager size of nanoparticles (Table 1a, $p<0.05$). When the amount of CS molecules exceeded that of local γ-PGA molecules, some of the excessive CS molecules were entangled onto the surfaces of CS-γ-PGA nanoparticles.

Thus, the resulting nanoparticles may display a structure of a neutral polyelectrolyte-complex core surrounded by a positively charged CS shell (Table 1b) ensuring the colloidal stabilization (Langmuir. 2004; 20:7766-7778). In contrast, as the amount of local γ-PGA molecules sufficiently exceeded that of surrounding CS molecules, the formed nanoparticles had γ-PGA exposed on the surfaces and thus had a negative charge of zeta potential. Therefore, the particle size and the zeta potential value of the prepared CS-γ-PGA nanoparticles can be controlled by their constituted compositions.

Figure 2:
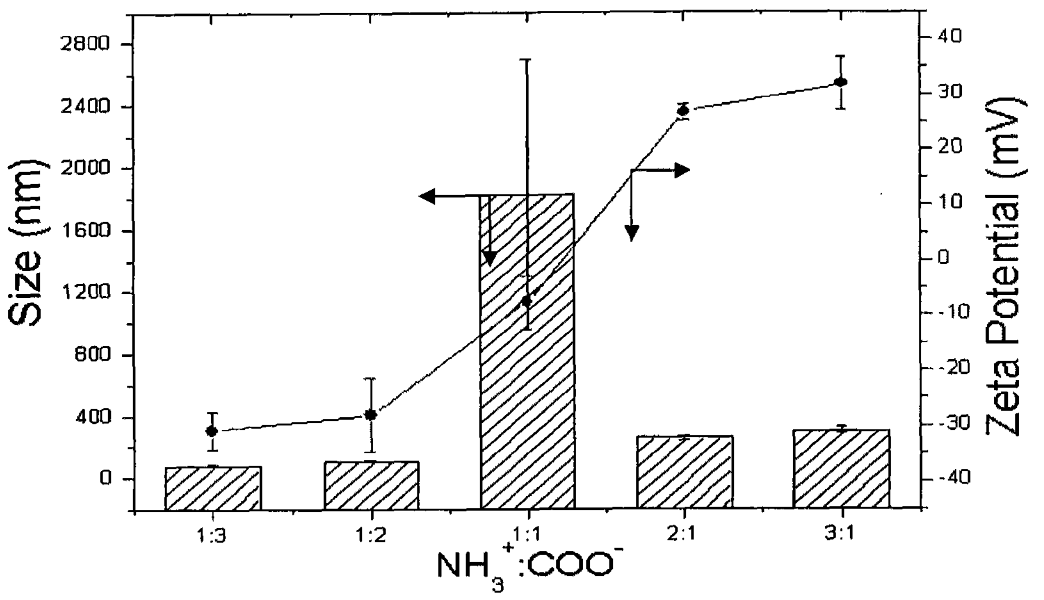
FIG. 2 shows particle size and zeta potential of the CS-γ-PGA nanoparticles encapsulated with pDNA.
Figure 3:
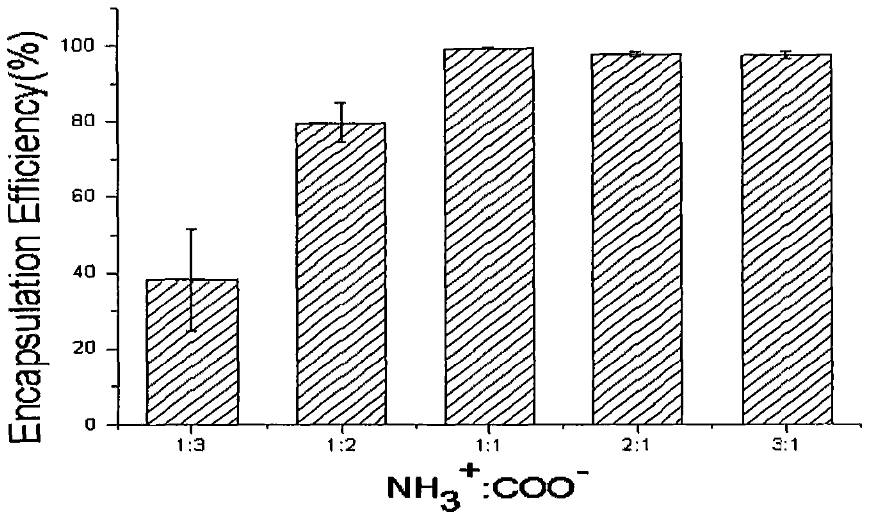
FIG. 3 shows the encapsulation efficiency of the CS-γ-PGA nanoparticles encapsulated with pDNA.

The size and zeta potential of the prepared nanoparticles increased with an increase of the ratio of $NH_3^+/COO^-$ (FIG. 2). The encapsulation efficiency of the prepared nanoparticles was less than 90% when the $NH_3^+/COO^-$ ratio was lower than 1.0 (FIG. 3). Some aspects of the invention relate to nanoparticles for transcutaneous or transdermal bombardment delivery processes having a mean particle size between about 50 and 500 nanometers, preferably between about 100 and 300 nanometers, and most preferably between about 150 and 250 nanometers. The morphology of the nanoparticles with encapsulated bioactive agents shows spherical in shape with a substantially smooth surface.

EXAMPLE NO. 6

Insulin Loading Capacity in Nanoparticles

TABLE 1a

Effects of concentrations of γ-PGA and CS on the particle sizes of the prepared CS-γ-PGA nanoparticles
Mean Particle Size (nm, n = 5)

| | CS | | | | |
|---|---|---|---|---|---|
| γ-PGA | 0.01% [a] | 0.05% | 0.10% | 0.15% | 0.20% |
| 0.01% [b] | 79.0 ± 3.0 | 103.1 ± 04.6 | 96.7 ± 1.9 | 103.6 ± 1.9 | 140.5 ± 2.0 |
| 0.05% | 157.4 ± 1.7 | 120.8 ± 3.9 | 144.5 ± 2.4 | 106.2 ± 3.8 | 165.4 ± 1.7 |
| 0.10% | 202.2 ± 3.1 | 232.6 ± 1.2 | 161.0 ± 1.8 | 143.7 ± 2.7 | 218.1 ± 04.1 |
| 0.15% | 277.7 ± 3.2 | 264.9 ± 2.1 | 188.6 ± 2.9 | 178.0 ± 2.2 | 301.1 ± 06.4 |
| 0.20% | 284.1 ± 2.1 | 402.2 ± 4.0 | ▲ | 225.5 ± 3.1 | 365.5 ± 5.1 |

[a] concentration of CS (by w/v)

[b] concentration of γ-PGA (by w/v)

▲ precipitation of aggregates was observed

TABLE 1b

Effects of concentrations of γ-PGA and CS on the zeta potential values of the prepared CS-γ-PGA nanoparticles.
Zeta Potential (mV, n =5)

| | CS | | | | |
|---|---|---|---|---|---|
| γ-PGA | 0.01% [a] | 0.05% | 0.10% | 0.15% | 0.20% |
| 0.01% [b] | 15.4 ± 0.3 | 22.8 ± 0.5 | 19.8 ± 1.5 | 16.5 ± 1.4 | 17.2 ± 1.6 |
| 0.05% | −32.7 ± 0.7 | 23.7 ± 1.7 | 27.6 ± 0.7 | 20.3 ± 0.8 | 19.2 ± 0.6 |
| 0.10% | −33.1 ± 1.3 | 21.1 ± 1.6 | 20.3 ± 1.1 | 23.6 ± 0.9 | 24.7 ± 1.2 |
| 0.15% | −33.2 ± 2.1 | −21.9 ± 2.0 | 19.2 ± 0.4 | 16.9 ± 1.7 | 19.8 ± 0.3 |
| 0.20% | −34.5 ± 0.5 | −34.6 ± 0.3 | ▲ | 14.6 ± 0.7 | 16.3 ± 0.7 |

[a] concentration of CS (by w/v)

[b] concentration of γ-PGA (by w/v)

▲ precipitation of aggregates was observed

The insulin-loaded CS-γ PGA nanoparticles are prepared by using the ionic-gelation method upon addition of insulin mixed with γ-PGA solution into CS solution, followed by magnetic stirring in a container. Model insulin used in the experiment and disclosed herein is obtained from bovine pancreas (Sigma-Aldrich, St. Louis, Mo.), having a molecular formula of $C_{254}H_{377}N_{65}O_{75}S_6$ with a molecular weight of about 5733.5 and an activity of ≧27 USP units/mg. The insulin contains two-chain polypeptide hormone produced by the β-cells of pancreatic islets. The α and β chains are joined by two interchain disulfide bonds. Insulin regulates the cellular uptake, utilization, and storage of glucose, amino acids, and fatty acids and inhibits the breakdown of glycogen, protein, and fat. The insulin from Sigma-Aldrich contains about 0.5% zinc. Separately, insulin can be obtained from other sources, such as human insulin solution that is chemically defined, recombinant from *Saccharomyces cerevisiae*. Some aspects of the invention relate to nanoparticles with insulin in the core, wherein the insulin may contain intermediate-acting, regular insulin, rapid-acting insulin, sustained-acting insulin that provides slower onset and longer duration of activity than regular insulin, or combinations thereof.

Examples of insulin or insulin analog products include, but not limited to, Humulin® (by Eli Lilly), Humalog® (by Eli Lilly) and Lantus® (by Aventis), and Novolog® Mix 70/30 (by Novo Nordisk, Denmark). Humalog (insulin lispro, rDNA origin) is a human insulin analog that is a rapid-acting, parenteral blood glucose-lowering agent. Chemically, it is Lys(B28), Pro(B29) human insulin analog, created when the amino acids at positions 28 and 29 on the insulin B-chain are reversed. Humalog is synthesized in a special non-pathogenic laboratory strain of *Escherichia coli* bacteria that has been genetically altered by the addition of the gene for insulin lispro. Humalog has the empirical formula $C_{257}H_{383}N_{65}O_{77}S_6$ and a molecular weight of 5808, identical to that of human insulin. The vials and cartridges contain a sterile solution of Humalog for use as an injection. Humalog injection consists of zinc-insulin lispro crystals dissolved in a clear aqueous fluid. Each milliliter of Humalog injection contains insulin lispro 100 Units, 16 mg glycerin, 1.88 mg dibasic sodium phosphate, 3.15 mg m-cresol, zinc oxide content adjusted to provide 0.0197 mg zinc ion, trace amounts of phenol, and water for injection. Insulin lispro has a pH of 7.0-7.8. Hydrochloric acid 10% and/or sodium hydroxide 10% may be added to adjust pH.

Humulin is used by more than 4 million people with diabetes around the world every day. Despite its name, this insulin does not come from human beings. It is identical in chemical structure to human insulin and is made in a factory using a chemical process called recombinant DNA technology. Humulin L is an amorphous and crystalline suspension of human insulin with a slower onset and a longer duration of activity (up to 24 hours) than regular insulin. Humulin U is a crystalline suspension of human insulin with zinc providing a slower onset and a longer and less intense duration of activity (up to 28 hours) than regular insulin or the intermediate-acting insulins (NPH and Lente).

LANTUS® (insulin glargine [rDNA origin] injection) is a sterile solution of insulin glargine for use as an injection. Insulin glargine is a recombinant human insulin analog that is a long-acting (up to 24-hour duration of action), parenteral blood-glucose-lowering agent. LANTUS is produced by recombinant DNA technology utilizing a non-pathogenic laboratory strain of *Escherichia coli* (K12) as the production organism. Insulin glargine differs from human insulin in that the amino acid asparagine at position A21 is replaced by glycine and two arginines are added to the C-terminus of the B-chain. Chemically, it is $21^A$-Gly-$30^B$a-L-Arg-$30^B$b-L-Arg-human insulin and has the empirical formula $C_{267}H_{404}N_{72}O_{78}S_6$ and a molecular weight of 6063.

LANTUS consists of insulin glargine dissolved in a clear aqueous fluid. Each milliliter of LANTUS (insulin glargine injection) contains 100 IU (3.6378 mg) insulin glargine. Inactive ingredients for the 10 mL vial are 30 mcg zinc, 2.7 mg m-cresol, 20 mg glycerol 85%, 20 mcg polysorbate 20, and water for injection. Inactive ingredients for the 3 mL cartridge are 30 mcg zinc, 2.7 mg m-cresol, 20 mg glycerol 85%, and water for injection.

Novolog® Mix 70/30 (70% insulin aspart protamine suspension and 30% insulin aspart injection [rDNA origin]) is a human insulin analog suspension. Novolog® Mix 70/30 is a blood glucose-lowering agent with a rapid onset and an intermediate duration of action. Insulin aspart is homologous with regular human insulin with the exception of a single substitution of the amino acid praline by aspartic acid in position B28, and is produced by recombinant DNA technology utilizing *Saccharomyces cerevisiae* as the production organism. Insulin aspart (Novolog) has the empirical formula $C_{256}H_{381}N_{65}O_{79}S_6$ and a molecular weight of 5826. Novolog® Mix 70/30 is a uniform, white sterile suspension that contains zinc 19.6 μg/ml and other components.

The nanoparticles with two insulin concentrations (at 0.042 and 0.083 mg/ml, respectively) are prepared at a chitosan to γ-PGA ratio of 0.75 mg/ml to 0.167 mg/ml. Their particle size and zeta potential are shown in Table 2 below.

TABLE 2

| Insulin Conc. (mg/ml) (n = 5) | Mean Particle Size (nm) | Polydispersity Index (PI) | Zeta Potential (mV) |
|---|---|---|---|
| 0* | 145.6 ± 1.9 | 0.14 ± 0.01 | +32.11 ± 1.61 |
| 0.042 | 185.1 ± 5.6 | 0.31 ± 0.05 | +29.91 ± 1.02 |
| 0.083 | 198.4 ± 6.2 | 0.30 ± 0.09 | +27.83 ± 1.22 |

(*) control reference without insulin

Figure 4:
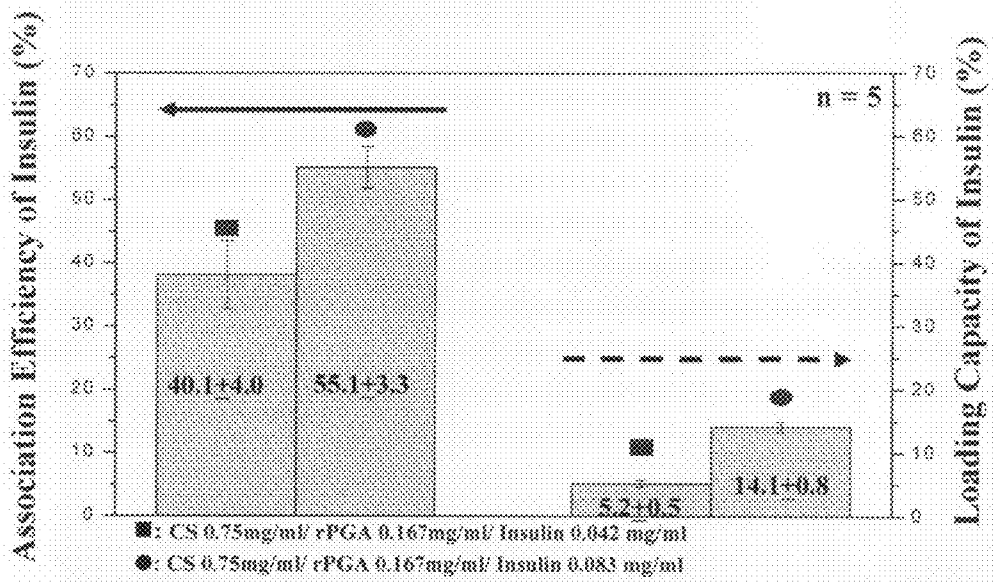
FIG. 4 shows loading capacity and association efficiency of insulin in nanoparticles made of chitosan and γ-PGA.
Figure 5:
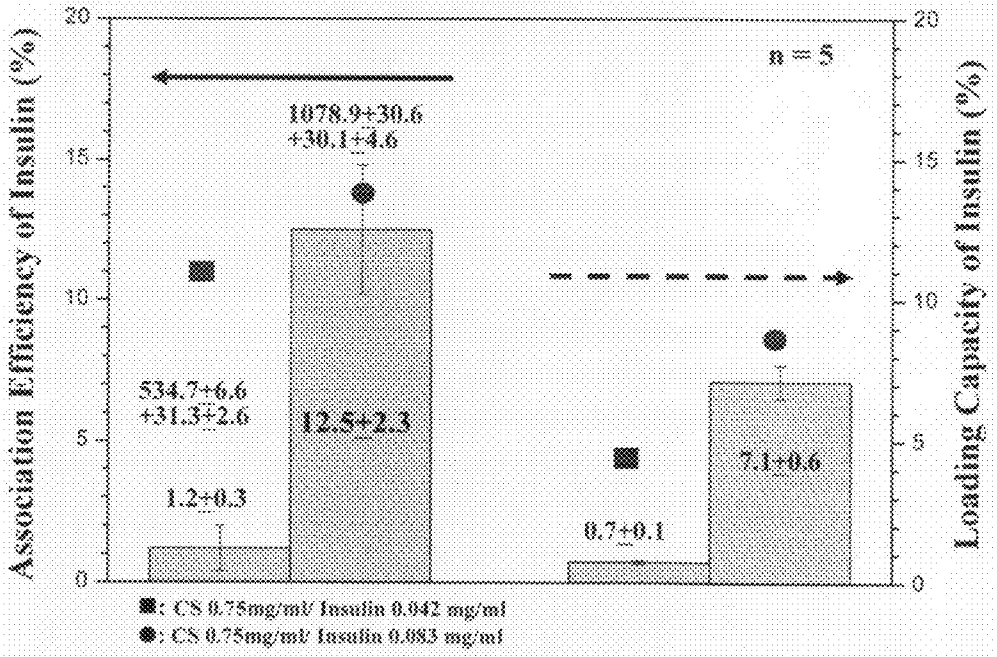
FIG. 5 shows loading capacity and association efficiency of insulin in nanoparticles made of chitosan as reference.

Further, their association efficiency (also known as loading efficiency) of insulin and loading capacity of insulin are analyzed, calculated and shown in FIGS. 4 and 5, according to the following formula:

$$\text{Insulin Association Efficiency } (AE\%) = \frac{(\text{Total amount of insulin} - \text{Insulin in supernatant})}{\text{Total amount of insulin}} \times 100\%$$

$$\text{Loading Capacity } (LC) = \frac{(\text{Total amount of insulin} - \text{Insulin in supernatant})}{\text{Weight of recovered particles}} \times 100\%$$

FIG. 4 shows the loading capacity and association efficiency of insulin in nanoparticles made of interacted chitosan and γ-PGA, whereas FIG. 5 shows the loading capacity and association efficiency of insulin in nanoparticles made of chitosan alone (in the absence of γ-PGA) as reference. The data clearly demonstrates that both the insulin loading capacity and insulin association efficiency are statistically higher for the nanoparticles with γ-PGA or a polyanionic compound in the core. The AE (40~55%) and LC (5.0~14.0%) of insulin for CS-γPGA nanoparticles was obtained by using an ionic-gelation method upon addition of insulin mixed with γ-PGA solution into CS solution, followed by magnetic stirring for nanoparticle preparation.

Some aspects of the invention relate to nanoparticles comprising a polyanionic component (such as γ-PGA, α-PGA, PGA derivatives, heparin, heparin analogs, low molecular weight heparin, glycosaminoglycans, alginate, or the like) in the core and low molecular weight chitosan in the shell, wherein the chitosan dominates on the surface of the nanoparticles with surface positive charges. In use, firstly, encapsulate the Alzheimer's drug in the chitosan shell nanoparticle as described herein, wherein the nanoparticle is partially crosslinked (optionally) to enhance its biodurability. Then transcutaneously or transdermally topical administer the nanoparticles via a nanoparticle nano-projectile bombardment process, whereby the nanoparticles migrate to the brain via capillary and artery circulation. The chitosan shell of certain intact nanoparticles adheres to the surface adjacent the tight junction in the brain. Thereafter, the chitosan nanoparticle opens the tight junction, wherein the Alzheimer's drug is released after passing the tight junction for therapeutic treatment. In one embodiment, the nanoparticles are in a spherical shape having a mean particle size of about 50 to 500 nanometers, preferably 150 nanometers to 250 nanometers.

In one example, transcutaneous or transdermal topical administration of the nanoparticles comprising chitosan shell substrate, polyanionic core substrate and at least one bioactive agent for treating Alzheimer's disease in a patient is typically performed with about 5 mg to 100 mg, preferably about 10 to 40 mg, of active agent per day over a period of one month to one year. The bioactive agent is selected from the group consisting of donepezile, rivastignine, galantamine, and/or those trade-named products, such as memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), and tacrine hydrochloride (Cognex® by Parke Davis).

Some aspects of the invention relate to a nanoparticle with a core substrate comprising polyglutamic acids such as water soluble salt of polyglutamic acids (for example, ammonium salt) or metal salts of polyglutamic acid (for example, lithium salt, sodium salt, potassium salt, magnesium salt, and the like). In one embodiment, the form of polyglutamic acid may be selected from the group consisting of poly-α-glutamic acid, poly-L-α-glutamic acid, poly-γ-glutamic acid, poly-D-glutamic acid, poly-γ-D-glutamic acid, poly-γ-DL-glutamic acid, poly-L-glutamic acid (manufactured by Sigma-Aldrich, St. Louis, Mo.), and PEG or PHEG derivatives of polyglutamic acid. Alginate is generally non-biodegradable; however, it is stipulated that an alginate particle with about 30-50 kDa molecular weight is kidney inert. Heparin with negatively charged side-groups has a general chemical structure as shown below:

Some aspects of the invention relate to the negatively charged glycosaminoglycans (GAGs) as the core substrate of the present nanoparticle formulation. GAGs may be used to complex with a low-molecular-weight chitosan to form drug-carrier nanoparticles. GAGs may also conjugate with the protein drugs or bioactive agents (including nucleic acid such as DNA, RNA, siRNA, and genes) as disclosed herein to enhance the bonding efficiency of the core substrate in the nanoparticles. Particularly, the negatively charged core substrate (such as GAGs, heparin, PGA, alginate, and the like) of the nanoparticles of the present invention may conjugate with chondroitin sulfate, hyaluronic acid, PDGF-BB, BSA, EGF, MK, VEGF, KGF, bFGF, aFGF, MK, PTN, etc.

EXAMPLE NO. 7

Insulin Nanoparticle Stability

Figure 6:
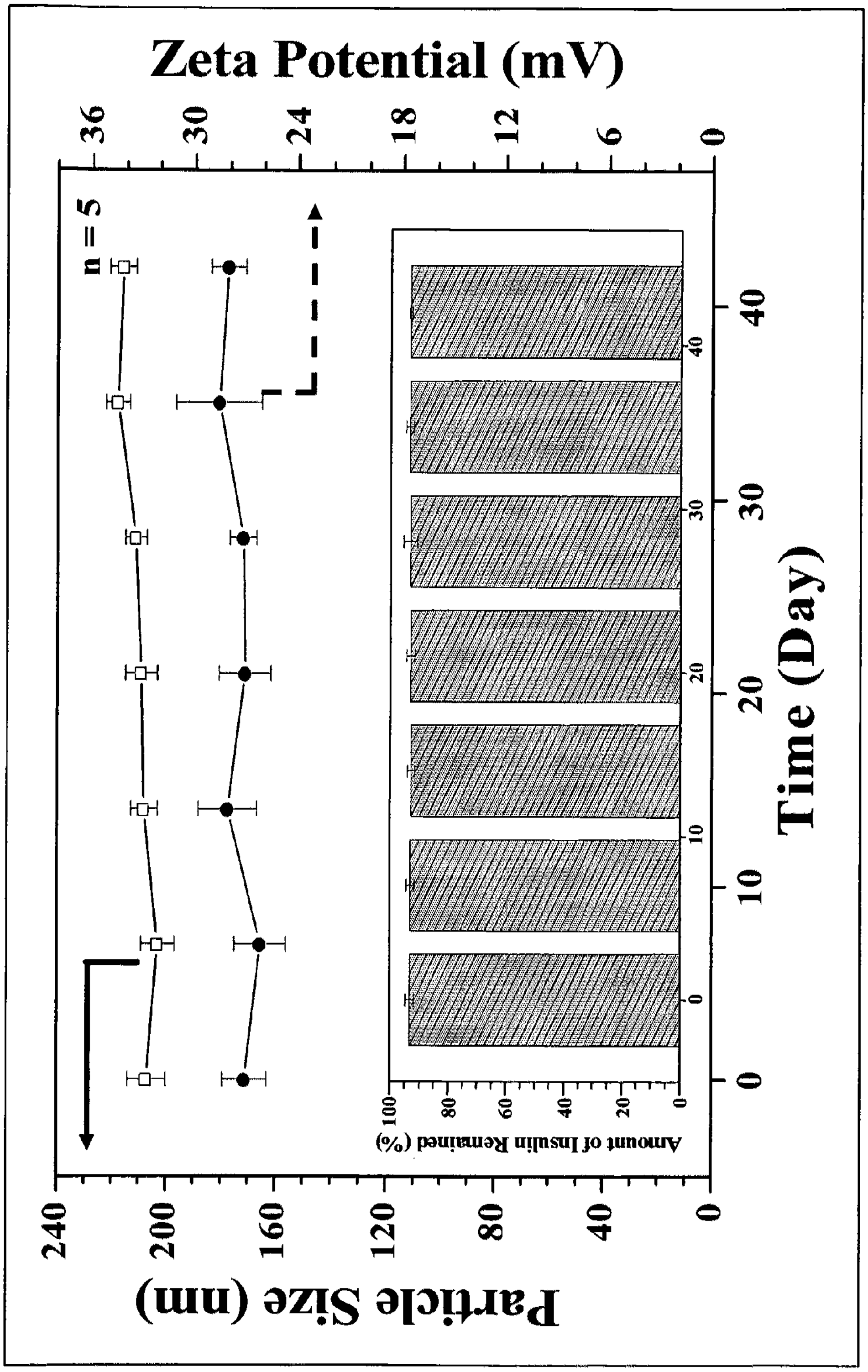
FIG. 6 shows the stability of insulin-loaded nanoparticles.

FIG. 6 shows the stability of insulin-loaded nanoparticles of the present invention with an exemplary composition of CS 0.75 mg/ml, γ-PGA 0.167 mg/ml, and insulin 0.083 mg/ml in the manufacturing process. The prepared insulin-loaded nanoparticles suspended in deionized water are stable during storage up to 40 days. Firstly (in FIG. 6), the insulin content in the nanoparticle storage solution maintains at about a constant level of 9.5%. The nanoparticle stability is further evidenced by the substantially constant particle size at about 200 nm and substantially constant zeta potential of about +28 mV over the period of about 40 days. It is contemplated that the insulin-containing nanoparticles of the present invention would further maintain their biostability when formulated in a soft gelcap configuration that further isolates the nanoparticles from environmental effects, such as sunlight, heat, air conditions, contaminants, and the like. Some aspects of the invention provide a gelcap capsule containing a dosage of insulin nanoparticles effective amount of the insulin to treat or manage the diabetic patients, wherein the stability of the insulin-containing nanoparticles is at least 40 days, preferably more than 6 months, and most preferably more than a couple of years. By "effective amount of the insulin", it is meant that a sufficient amount of insulin would be present in the dose to provide for a desired therapeutic, prophylatic, or other biological effect when the compositions are administered to a host in the single dosage forms.

EXAMPLE NO. 8

In Vivo Study with Insulin-Loaded Fluorescence-Labeled Nanoparticles

In the in vivo study, rats were injected with streptozotocin (STZ 75 mg/kg intraperitoneal) in 0.01M citrate buffer (pH 4.3) to induce diabetes rats. The blood from the rat's tail was analyzed with a commercially available glucometer for blood glucose. The blood glucose level on Wistar male rats at no fasting (n=5) is measured at 107.2±8.1 mg/dL for normal rats

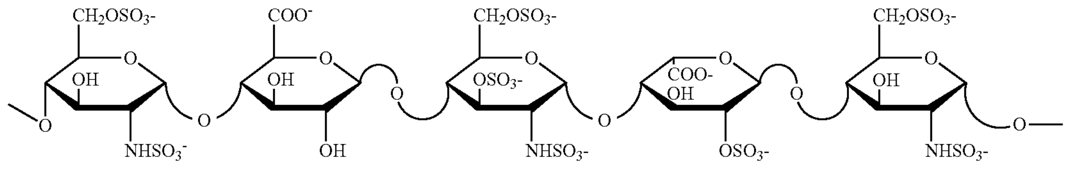

while the blood glucose level is at 469.7±34.2 mg/dL for diabetic rats. In the animal study, diabetic rats were fasting for 12 hours and subjected to four different conditions: (a) oral deionized water (DI) administration; (b) oral insulin administration at 30 U/kg; (c) oral insulin-loaded nanoparticles administration at 30 U/kg; and (d) subcutaneous (SC) insulin injection at 5 U/kg as positive control. The blood glucose concentration from rat's tail was measured over the time in the study.

Figure 7:
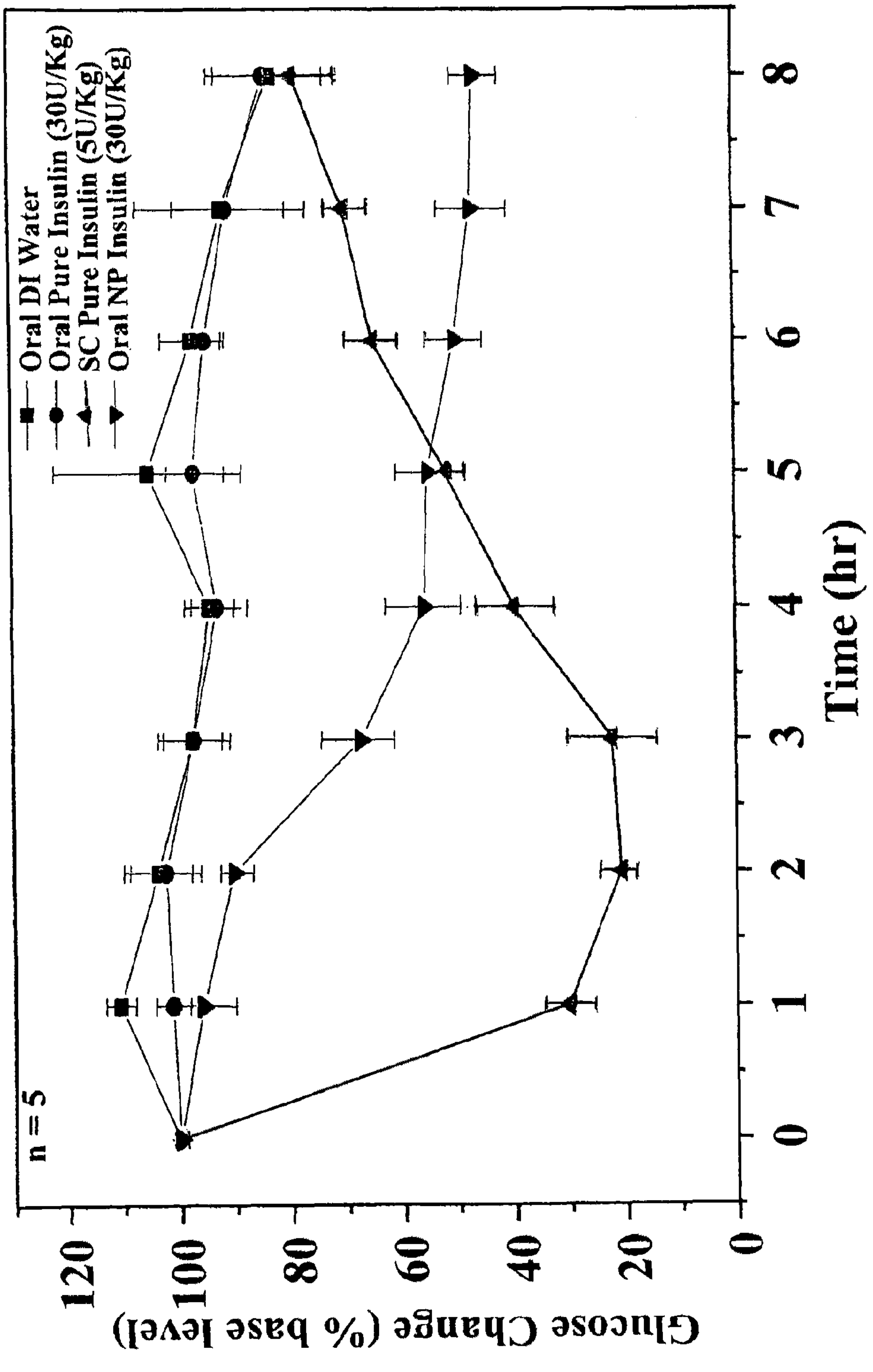
FIG. 7 shows the bioavailability of insulin of administered insulin-loaded nanoparticles in diabetic rats.

FIG. 7 shows glucose change (hypoglycemic index) versus time of the in vivo animal study (n=5). The glucose change as a percentage of baselines for both oral DI administration and oral insulin administration over a time interval of 8 hours appears relatively constant within the experimental measurement error range. It is illustrative that substantially all insulin from the oral administration route has been decomposed in rat stomach. As shown, the glucose decrease for the SC insulin injection route appears in rat blood in the very early time interval and starts to taper off after 3 hours in this exemplary study. The most important observation of the study comes from the oral administration route with insulin-loaded nanoparticles. The blood glucose begins to decrease from the base line at about 2 hours after administration and sustains at a lower glucose level at more than 8 hours into study. Regarding oral administration route with insulin-loaded nanoparticles of the present invention, several repeated rat insulin studies (not shown here) confirmed sustained effects of lower glucose levels for up to 24 hours. It suggests that the current insulin-loaded nanoparticles modulate the glucose level in animals in a sustained or prolonged effective mode.

Some aspects of the invention relate to a novel nanoparticle system that is composed of a low-MW CS and γ-PGA with CS dominated on the surfaces. The surface of the nanoparticles is characterized with a positive surface charge. In one embodiment, the nanoparticles of the invention enables effective delivery for bioactive agent, including peptide, polypeptide, protein drugs, other large hydrophilic molecules, DNA, RNA, genes, and the like. Such polypeptide drugs can be any natural or synthetic polypeptide that may be administered to a human patient. Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors: interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; vaccines; monoclonal antibodies; and the like; and analogs and derivatives of these compounds. The bioactive agent of the present invention may be selected from group consisting of oxytocin, vasopressin, adrenocorticotrophic hormone, prolactin, luliberin or luteinising hormone releasing hormone, growth hormone, growth hormone releasing factor, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies, bacteriophages, and soluble vaccines.

EXAMPLE NO. 9

Nanoparticles Loaded with Calcitonin

Calcitonin is a protein drug that serves therapeutically as calcium regulators for treating osteoporosis (J. Pharm. Pharmacol. 1994; 46:547-552). Calcitonin has a molecular formula of $C_{145}H_{240}N_{44}O_{48}S_2$ with a molecular weight of about 3431.9 and an isoelectric point of 8.7. The net charge for calcitonin at pH 7.4 is positive that is suitable to complex or conjugate with negatively charged core substrate, such as γ-PGA or α-PGA. In preparation, nanoparticles were obtained upon addition of a mixture of γ-PGA plus calcitonin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Supernatants were discarded and nanoparticles were resuspended in deionized water as the solution products, further encapsulated in soft gels or further treated with an enteric coating. Nanoparticles with complexed calcitonin or other calcium regulators for treating osteoporosis appears a candidate for transcutaneous or transdermal administration to a patient via the suggested nanoparticle projectile bombardment route as discussed herein.

EXAMPLE NO. 10

Nanoparticles Loaded with Vancomycin

Vancomycin is a protein drug that serves therapeutically as antibiotic against bacterial pathogens. Vancomycin has a molecular formula of $C_{66}H_{75}N_9O_{24}$ with a molecular weight of about 1485.7 and an isoelectric point of 5.0. The net charge for vancomycin at pH 7.4 is negative that is suitable to complex or conjugate with a portion of negatively charged shell substrate, such as chitosan. In preparation, nanoparticles were obtained upon addition of a mixture of γ-PGA plus vancomycin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature, wherein CS concentration is provided sufficiently to conjugate vancomycin, to counterbalance γ-PGA, and exhibit positive surface charge for the nanoparticles with excess non-conjugated CS. Nanoparticles were collected by ultracentrifugation at 38,000 rpm for 1 hour. Supernatants were discarded and nanoparticles were resuspended in deionized water as the solution products, further encapsulated in soft gels or further treated with an enteric coating. Nanoparticles with conjugated vancomycin or other antibiotics appears a candidate for transcutaneous or transdermal administration to a patient via the suggested nanoparticle projectile bombardment gun route as discussed herein.

Some aspects of the invention relate to a method of delivering at least one bioactive agent to a patient comprising administering nanoparticles composed chitosan (or of γ-PGA and chitosan) via topical transcutaneous or transdermal or targeted epidermal/transdermal routes using a nanoparticle bombardment gun, wherein the nanoparticles are loaded with a therapeutically effective amount or dose of the at least one bioactive agent. In a preferred embodiment, the nanoparticles are biodegradable. In another embodiment, the nanoparticles are made of biodegradable polymer selected from the group consisting of poly(L-lactic acid), polyglycolic acid, poly (D,L-lactide-co-glycolide), poly (ester amides), polycaprolactone, co-polymers thereof, and the like. The biodegradable polymer comprises a biodegradable linkage selected from the group consisting of ether groups, ester groups, carbonate groups, amide groups, anhydride groups, and orthoester groups. By way of example, poly(ester amides), particularly poly[(8-L-Leu-6)$_3$-(8-L-Lys(Bz))$_1$], is well known to one skilled in the art that has been disclosed in U.S. Pat. No. 5,485,496 and elsewhere. Suitable biodegradable polymer to be used in the present invention can be found in Handbook of Biodegradable Polymers by Domb et al. (Harwood Academic Publishers: Amsterdam, The Netherlands 1997). Preferably, the materials have been approved by the U.S. Food and Drug Administration.

The nanoparticle of the present invention is an effective delivery system for peptide and protein drugs and other hydrophilic molecules. In a further embodiment, the bioactive agent is selected from the group consisting of proteins, peptides, nucleosides, nucleotides, antiviral agents, antineoplastic agents, antibiotics, and anti-inflammatory drugs. In a further embodiment, the bioactive agent is selected from the group consisting of calcitonin, cyclosporin, insulin, oxytocin, tyrosine, enkephalin, tyrotropin releasing hormone (TRH), follicle stimulating hormone (FSH), luteinizing hormone (LH), vasopressin and vasopressin analogs, catalase, superoxide dismutase, interleukin-II (IL-2), interleukin-11 (IL-11), interferon, colony stimulating factor (CSF), tumor necrosis factor (TNF), tumor necrosis factor inhibitor, and melanocyte-stimulating hormone. In a further embodiment, the bioactive agent is an Alzheimer antagonist. In another embodiment, the bioactive agent is a gene or a DNA.

EXAMPLE NO. 11

Nanoparticles Loaded with Heparin Core Substrate

Heparin is a negatively charged drug that serves therapeutically as anti-coagulant. Heparin is generally administered by intravenous injection. Some aspects of the invention relate to heparin nanoparticles for topical administration or subcutaneous/transcutaneous or transdermal administration using a nanoparticle projectile bombardment gun. In a further embodiment, heparin serves as at least a portion of the core substrate with chitosan as shell substrate, wherein heparin conjugates with at least one bioactive agent as disclosed herein. In preparation, nanoparticles were obtained upon addition of heparin Leo aqueous solution (2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature. Nanoparticles were collected by ultracentrifugation at 38,000 rpm for 1 hour. Table 3 shows the conditions of solution preparation and the average nanoparticle size.

TABLE 3

| Conditions | Heparin conc. @ 2 ml | Chitosan conc. @ 10 ml | Particle size (nm) |
|---|---|---|---|
| A | 200 iu/ml | 0.09% | 298.2 ± 9.3 |
| B | 100 iu/ml | 0.09% | 229.1 ± 4.5 |
| C | 50 iu/ml | 0.09% | 168.6 ± 1.7 |
| D | 25 iu/ml | 0.09% | 140.1 ± 2.3 |

To evaluate the pH stability of the heparin-containing nanoparticles from Example no. 11, the nanoparticles from Condition D in Table 3 are subjected to various pH for 2 hours (sample size=7). Table 4 shows the average size, size distribution (polydispersity index: PI) and zeta potential (Zeta) of the nanoparticles at the end of 2 hours under various pH environments. The data shows that the nanoparticles are relatively stable. In one embodiment, the nanoparticles of the present invention may include heparin, heparin sulfate, small molecular weight heparin, and heparin derivatives.

TABLE 4

| pH | 1.5 | 2.6 | 6.6 | 7.4 | Deionized water @ 5.9 |
|---|---|---|---|---|---|
| Size (nm) | 150 ± 9 | 160 ± 12 | 153 ± 2 | 154 ± 4 | 147 ± 5 |
| PI | 0.54 ± 0.03 | 0.50 ± 0.04 | 0.08 ± 0.02 | 0.32 ± 0.03 | 0.37 ± 0.02 |
| Zeta (+) | 15 ± 2 | 33 ± 6 | 15 ± 0.1 | 11 ± 0.2 | 18 ± 4 |

In a further embodiment, a growth factor such as bFGF with pharmaceutically effective amount is added to heparin Leo aqueous solution before the pipetting step in Example No. 11. In our laboratory, growth factors and proteins with pharmaceutically effective amount have been conjugated with heparin to form nanoparticles of the present invention with chitosan as the shell substrate, wherein the growth factor is selected from the group consisting of Vascular Endothelial Growth Factor (VEGF), Vascular Endothelial Growth Factor 2 (VEGF2), basic Fibroblast Growth Factor (bFGF), Vascular Endothelial Growth Factor 121 (VEGF121), Vascular Endothelial Growth Factor 165 (VEGF165), Vakular Endothelial Growth Factor 189 (VEGF189), Vascular Endothelial Growth Factor 206 (VEGF206), Platelet Derived Growth Factor (PDGF), Platelet Derived Angiogenesis Factor (PDAF), Transforming Growth Factor-β (TGF-β), Transforming Growth Factor-α (TGF-α), Platelet Derived Epidermal Growth Factor (PDEGF), Platelet Derived Wound Healing Formula (PDWHF), epidermal growth factor, insulin-like growth factor, acidic Fibroblast Growth Factor (aFGF), human growth factor, and combinations thereof; and the protein is selected from the group consisting of haemagglutinin (HBHA), Pleiotrophin, buffalo seminal plasma proteins, and combinations thereof.

It is suggested that a biomaterial with free amino groups of lysine, hydroxylysine, or arginine residues within biologic tissues is crosslinkable with genipin, a crosslinker (Biomaterials 1999; 20:1759-72). It is also suggested that the crosslinkable biomaterial may be crosslinked with a crosslinking agent or with light, such as ultraviolet irradiation, wherein the crosslinkable biomaterial may be selected from the group consisting of collagen, gelatin, elastin, chitosan, NOCC (N, O, carboxylmethyl chitosan), fibrin glue, biological sealant, and the like. Further, it is disclosed that a crosslinking agent may be selected from the group consisting of genipin, its derivatives, analog (for example, aglycon geniposidic acid), stereoisomers and mixtures thereof. In one embodiment, the crosslinking agent may further be selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers, and the like.

In one embodiment, it is disclosed that loading drug onto a chitosan-containing biological material crosslinked with genipin or other crosslinking agent may be used as biocompatible drug carriers for drug slow-release or sustained release. Several biocompatible plastic polymers or synthetic polymers have one or more amine group in their chemical structures, for example poly(amides) or poly(ester amides). The amine group may become reactive toward a crosslinking agent, such as glutaraldehyde, genipin or epoxy compounds of the present invention. In one embodiment, the nanoparticles comprised of crosslinkable biomaterial is crosslinked, for example up to about 50% degree or more of crosslinking, preferably about 1 to about 20% degree of crosslinking of the crosslinkable components of the biomaterial, enabling sustained biodegradation of the biomaterial and/or sustained drug release. The degree of crosslinking (DofC) is calculated from the following equation, where the crosslinkable site is referred to the number of amino group (—$NH_3^+$) sites on chitosan:

$$DofC=(1-\text{remaining available amino group sites/total amino group sites})\times 100$$

By modifying the chitosan structure to alter its charge characteristics, such as grafting the chitosan with methyl, N-trimethyl, alkyl (for example, ethyl, propyl, butyl, isobutyl, etc.), or N-palmitoy, polyethylene glycol (PEG), or heparin (including low molecular weight heparin, regular molecular weight heparin, and genetically modified heparin), the surface charge density (zeta potential) of the CS-γ PGA nanoparticles may become more pH resistant or more hydrophilic.

Transdermal DNA Delivery

Gold particles have been conventionally used as a carrier for transdermal gene delivery, which may cause adverse side effects when accumulated. One aspect of the invention relates to biodegradable nanoparticles (NPs), composed of chitosan (CS) and poly-γ-glutamic acid (γ-PGA), that are prepared by an ionic-gelation method for transdermal "nucleic acid" (such as DNA, RNA, gene, siRNA and the like) delivery via CS/γ-PGA/DNA NPs using a low-pressure gene gun. The conventional CS/DNA NPs (coded 'control NPs') without the incorporation of γ-PGA are used as control to demonstrate enhanced effects of the newly disclosed CS/γ-PGA/DNA NPs (coded 'test NPs') in transdermal DNA delivery. In one embodiment, the transdermal siRNA delivery uses nanoparticles comprised of CS/γ-PGA/siRNA following the similar description of the CS/γ-PGA/DNA NPs by using a low-pressure gene gun. Small-angle X-ray scattering (SAXS) is used to examine the internal structures of test NPs (that is, the CS/γ-PGA/DNA NPs or the CS/γ-PGA/siRNA NPs), while identification of their constituents is conducted by Fourier transformed infrared (FT-IR) spectroscopy. The CS/γ-PGA/DNA NPs are substantially spherical (spheroidal) in shape with a relatively homogeneous size distribution.

In contrast, CS/DNA NPs have a heterogeneous size distribution with a donut, rod or pretzel shape. Both newly developed test NPs and control NPs are able to effectively retain the encapsulated DNA and protect it from nuclease degradation. As compared with control CS/DNA NPs, the newly developed CS/γ-PGA/DNA NPs improve their penetration depth into the mouse skin and enhance gene expression. These observations may be attributed to the fact that CS/γ-PGA/DNA NPs are more compact in their internal structures and have a greater density than their CS/DNA counterparts, thus having a larger momentum to penetrate into the skin barrier. The results reveal that CS/γ-PGA/DNA NPs could substitute gold particles as a DNA carrier for transdermal gene delivery. Similarly, it was demonstrated that the transdermal siRNA delivery might use nanoparticles comprised of CS/γ-PGA/siRNA for transdermal gene delivery.

Nanoparticles Loaded with Plasmid DNA

Plasmids (pEGFP-N2, 4.7 kb) containing a CMV promoter and an enhanced green fluorescence protein reporter (EGFP reporter) were obtained from BD Biosciences Clontech (Palo Alto, Calif., USA). pEGFP-N2 was amplified and isolated using a Plasmid Mega Kit (QIAGEN, Valencia, Calif., USA). The recovered plasmids were stored at 4° C. in sterile deionized (DI) water. The purity of plasmids was analyzed by gel electrophoresis (0.8% agarose), while their concentration was measured by UV absorption at 260 nm (V-530, Jasco, Tokyo, Japan). One aspect of the invention relates to preparation of the NPs (i.e., CS/γ-PGA/DNA NPs) encapsulated with a plasmid DNA containing a reporter gene. Physicochemical characteristics of the prepared NPs were examined by Fourier transformed infrared (FT-IR) spectroscopy and transmission electron microscopy (TEM) as well as small angle X-ray scattering (SAXS) and dynamic light scattering (DLS) measurements. Additionally, the penetration depth of the prepared NPs bombarded by a low-pressure gene gun and their gene expression in a mouse model are disclosed herein. The conventional CS/DNA NPs without the incorporation of γ-PGA were used as reference.

RNA and DNA are both nucleic acids, but differ in three main ways. First, unlike DNA that is double-stranded, RNA is a single-stranded molecule in most of its biological roles and has a much shorter chain of nucleotides. Second, while DNA contains deoxyribose, RNA contains ribose, (there is no hydroxyl group attached to the pentose ring in the 2' position in DNA). These hydroxyl groups make RNA less stable than DNA because it is more prone to hydrolysis. Third, the complementary base to adenine is not thymine, as it is in DNA, but rather uracil, which is an unmethylated form of thymine.

A nucleic acid is a macromolecule composed of chains of monomeric nucleotides. In biochemistry, these molecules carry genetic information or form structures within cells. The most common nucleic acids are deoxyribonucleic acid (DNA) and ribonucleic acid (RNA). Nucleic acids are universal in living things, as they are found in all cells and viruses. Artificial nucleic acids include peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule.

Preparation of DNA-Loaded NPs

The charge ratio (N/C/P) of NPs was expressed as the ratio of moles of the amino groups (N) on CS to the carboxyl groups (C) on γ-PGA and the phosphate groups (P) on DNA or siRNA. Test NPs at various known N/C/P molar ratios (study groups of 8:0:1, 8:1:1, 8:2:1, 8:4:1 and 8:6:1) were prepared by an ionic-gelation method. By ways of illustration, an aqueous DNA (pEGFP-N2, 33 μg) was mixed with an aqueous γ-PGA (20 kDa, Vedan, Taichung, Taiwan) at different concentrations (12.8 μg, 25.6 μg, 51.2 μg or 76.8 μg, final volume 80 μl). NPs were obtained upon addition of the mixed solution, using a pipette, into an aqueous CS (80 kDa, 0.4 μg/μl, 400 μl, pH 6.0, Challenge Bioproducts, Taichung, Taiwan). The solutions were thoroughly mixed for 10-15 seconds and left for at least 1 hour at room temperature. NPs were collected by centrifugation at 14,000 rpm for 30 min. Supernatants were discarded and NPs were resuspended in DI water at pH 6.0 for further studies.

Characteristics of DNA-Loaded NPs

The pKa values of CS and γ-PGA are 6.5 and 2.9, respectively. In DI water (pH 6.0), CS and γ-PGA are in ionized forms. The ionized CS, γ-PGA and DNA can form polyelectrolyte complexes (CS/γ-PGA/DNA NPs) by ionic interactions between the positively charged amino groups (—$NH_3^+$) on CS and the negatively charged carboxyl groups (—$COO^-$) on γ-PGA and phosphate groups (—$PO_4^-$) on DNA. The particle size, polydispersity index, zeta potential and DNA encapsulation efficiency of NPs prepared at varying N/C/P molar ratios, obtained by DLS, are shown in Table 5. It can be seen that the prepared NPs are in the nanometer scale (150-250 nm) with a positively charged zeta potential. With increasing amount of the negatively charged γ-PGA, the positively charged zeta potential of NPs decreases.

Figure 10:
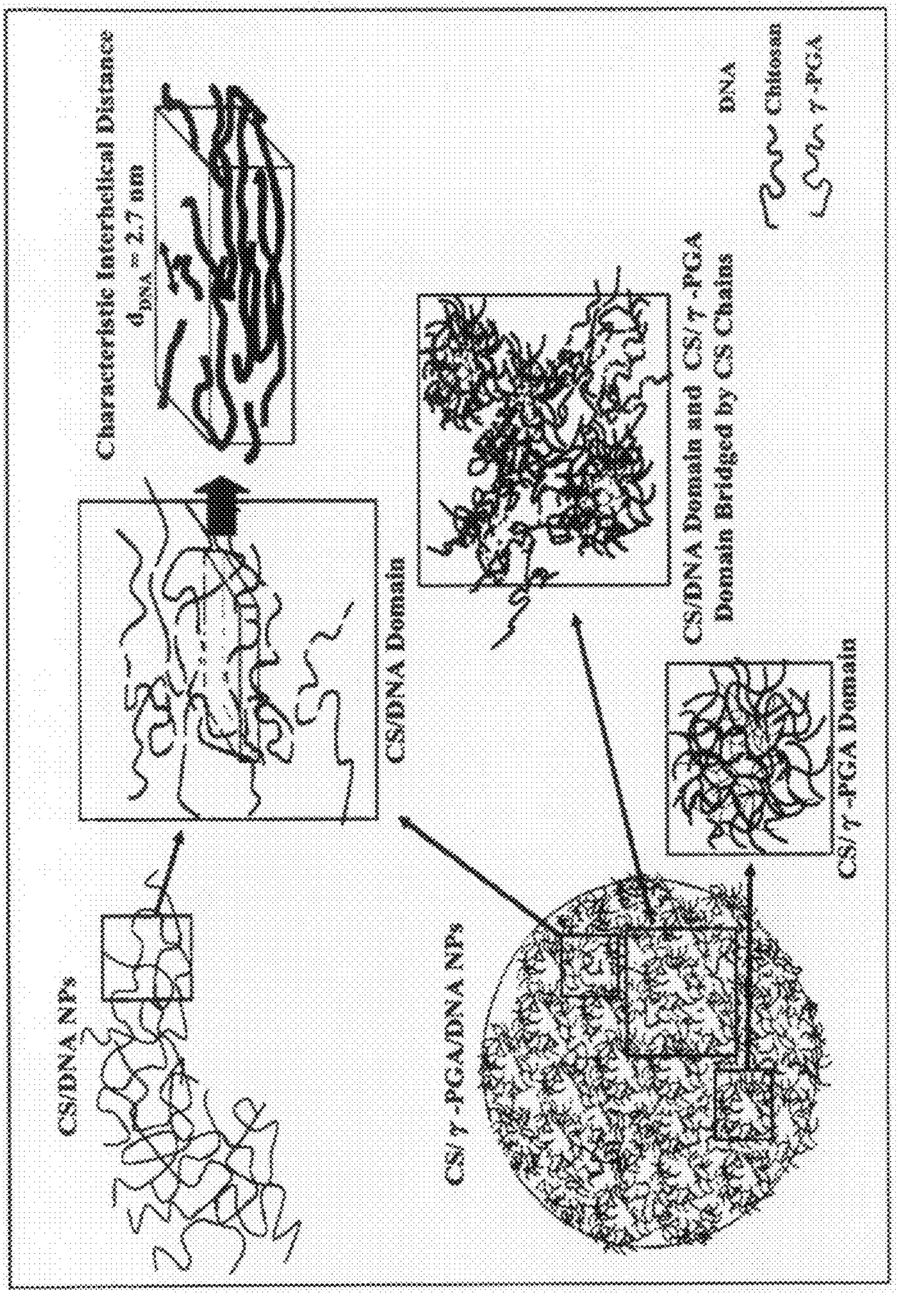
FIG. 10 shows schematic illustrations of the internal structures of CS/DNA NPs and CS/γ-PGA/DNA NPs. chitosan; γ-PGA: poly-γ-glutamic acid; NPs: nanoparticles.

The encapsulation efficiencies of DNA in the NPs prepared at distinct N/C/P ratios are about the same and approached 100%, even with the incorporation of the negatively charged γ-PGA. Among all study groups, the NPs prepared at an N/C/P ratio of 8:4:1 have the smallest polydispersity index. Polydispersity index, obtained by the photon correlation spectroscopy analysis, is a parameter defining the particle size distribution of NPs. It is a dimensionless number extrapolated from the autocorrelation function and ranges from a value of 0.01 for monodispersed particles up to a value around 0.5-0.7. A value greater than 0.7 is characteristic of samples with a very broad size distribution. For a better control of transdermal DNA delivery or for gene expression, the NPs prepared at an N/C/P ratio of 8:4:1, which display the smallest size distribution among all study groups, were chosen for further studies. However, the NPs at N/C/P ratio range of 8:1:1 to 8:6:1 all show favorably a PI of between about 0.45 and 0.1 and an average particle size of between about 200 nm and 100 nm.

system containing CS, γ-PGA, and DNA appear to be the superposition of the two scattering curves of CS/DNA and CS/γ-PGA complexes. In this case, the DNA-DNA correlation peak from the CS/DNA complex is partly masked by the monotonically decayed profile loaded with the CS/γ-PGA complex. However, the position of this peak is essentially identical with that found for the binary CS/DNA NPs. The observed scattering feature hence attests that DNA and γ-PGA complexed rather independently with CS in the solution and the internal structures of the respective complexes closely resemble those formed in the corresponding binary systems. It is proposed that the individual NPs formed through the complexation in the ternary system actually consist of two types of domains, namely, the CS/γ-PGA complex domain and the CS/DNA complex domain in which the DNA chains are closely packed, as schematically illustrated in FIG. 10.

The independent complexation behavior of γ-PGA and DNA is likely due to their different complexation kinetics loaded with different concentrations of γ-PGA and DNA as well as different activation barriers involving the losses of conformational and translational entropies of the polymer chains upon complexation. At the instant of mixing, complexation of CS with γ-PGA might likely take place earlier than that with DNA due to the higher reactant concentration of γ-PGA. Since the amount of CS is higher than the stoichiometric value for complexation with γ-PGA, the presence of unbounded segments or sub-chains of CS at or emanating from the surface of CS/γ-PGA complex particles is expected.

TABLE 5

Particle size (nm), polydispersity index (PI), zeta potential (mV) and encapsulation efficiency (EE, %) of CS/DNA or CS/γ-PGA/DNA nanoparticles prepared at varying N/C/P molar ratios (n = 5). CS: chitosan; γ-PGA: poly-γ-glutamic acid.

| N/C/P Ratio | 8:0:1 | 8:1:1 | 8:2:1 | 8:4:1 | 8:6:1 |
|---|---|---|---|---|---|
| Particle Size | 229.3 ± 29.2 | 174.5 ± 12.1 | 146.0 ± 8.6 | 146.6 ± 10.2 | 173.9 ± 14.7 |
| PI | 0.54 ± 1.81 | 0.43 ± 0.15 | 0.28 ± 0.09 | 0.14 ± 0.03 | 0.17 ± 0.05 |
| Zeta Potential | 36.2 ± 0.5 | 34.3 ± 0.8 | 32.9 ± 1.5 | 20.6 ± 0.8 | 16.4 ± 1.4 |
| EE | 98.4 ± 1.9 | 97.0 ± 2.5 | 96.8 ± 3.1 | 98.1 ± 1.4 | 98.5 ± 1.2 |

Figure 9:
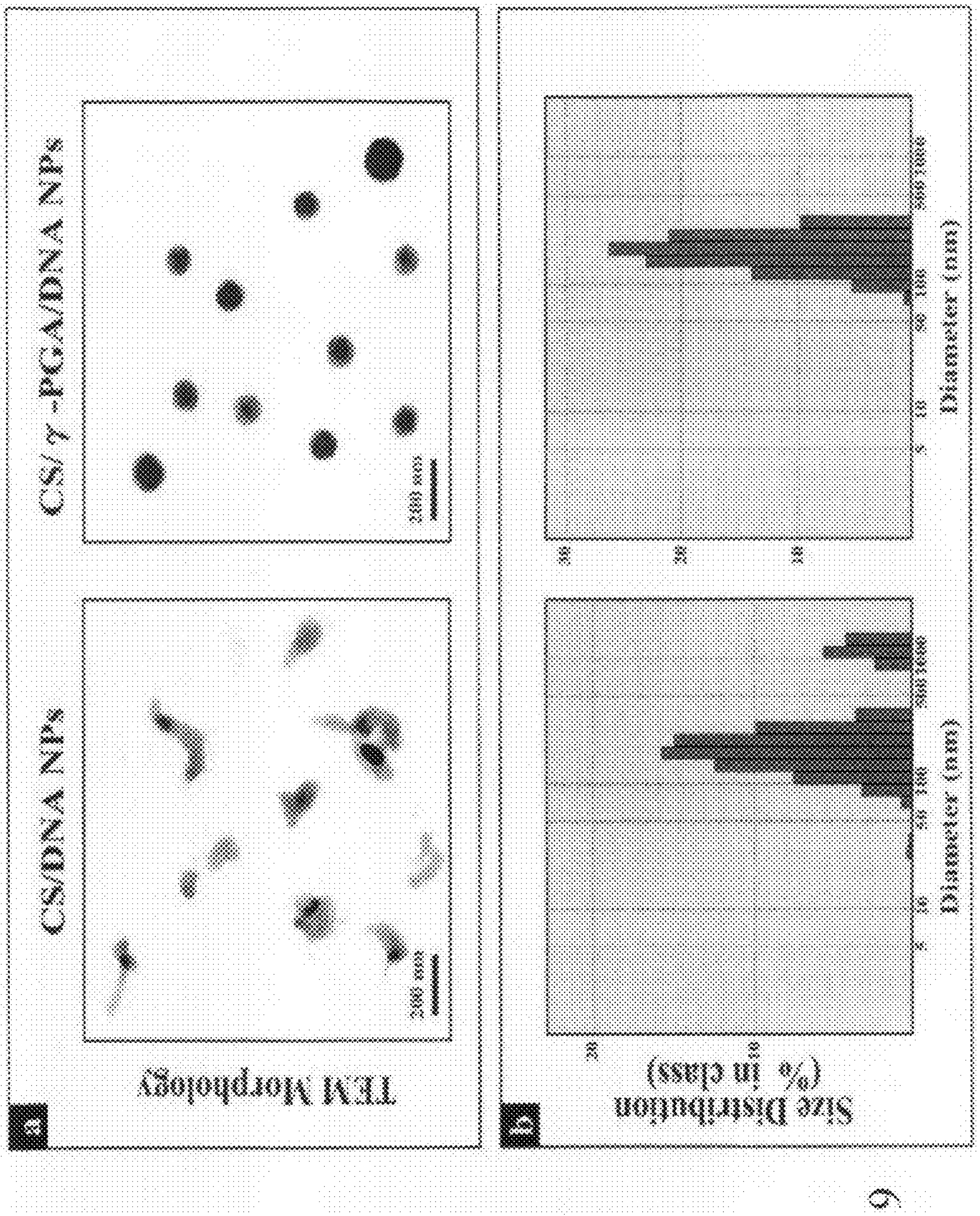
FIG. 9 shows (a) TEM micrographs of CS/DNA and CS/γ-PGA/DNA NPs; (b) size distribution of CS/DNA and CS/γ-PGA/DNA NPs obtained by dynamic light scattering. CS: chitosan; γ-PGA: poly-γ-glutamic acid; NPs: nanoparticles.

In one embodiment, the CS/γ-PGA/DNA NPs (N/C/P ratio of 8:4:1) prepared in DI water (pH 6.0) are spherical in shape with a relatively homogeneous size distribution (FIGS. 9*a* and 9*b*). In contrast, CS/DNA NPs (N/C/P ratio of 8:0:1) have a heterogeneous size distribution with a donut, rod or pretzel shape. Similar observation was also reported by other groups on the control CS/DNA NPs. Additionally, the CS/γ-PGA/DNA NPs appear to be more compact than CS/DNA NPs. All other CS/γ-PGA/DNA NPs (N/C/P ratio of 8:1:1 to 8:6:1) are all in spherical or spheroidal shape.

The diameters of NPs observed by TEM (FIG. 9*a*) (JEOL, Tokyo, Japan) are significantly smaller than those obtained by DLS (Table 5). This is because the diameters of NPs obtained by DLS reflect the hydrodynamic diameters of NPs swollen in aqueous solution, while those observed by TEM are the diameters of dried NPs.

Upon complexation, the CS polyelectrolyte chains tend to wrap around DNA due to electrostatic attraction; the bridging of a given CS chain across a number of DNA chains causes a significant aggregation of DNA. The locally stiff DNA chains in the complex then organize for ordered packing driven by their excluded volume interaction. The SAXS profile of the These segments might subsequently complex with the DNA chains, and the bridging between γ-PGA and DNA by CS chains might eventually lead to a compact internal structure within the NPs containing two types of domains.

Stability of DNA-Loaded NPs at Different pH Environments

No aggregation of CS/DNA NPs or CS/γ-PGA/DNA NPs during storage in DI water (pH 6.0) for at least 8 weeks is observed and changes in their particle size and zeta potential are minimal, as a result of the electrostatic repulsion between the positively charged NPs. Precipitation of particles is observed with time (within 2 weeks) for aqueous suspensions of CS/γ-PGA/DNA NPs but not for CS/DNA NPs, indicating that the density of CS/γ-PGA/DNA NPs is greater than that of CS/DNA NPs. However, the precipitated CS/γ-PGA/DNA NPs can be resuspended in DI water after a vigorous vortex.

Figure 11:
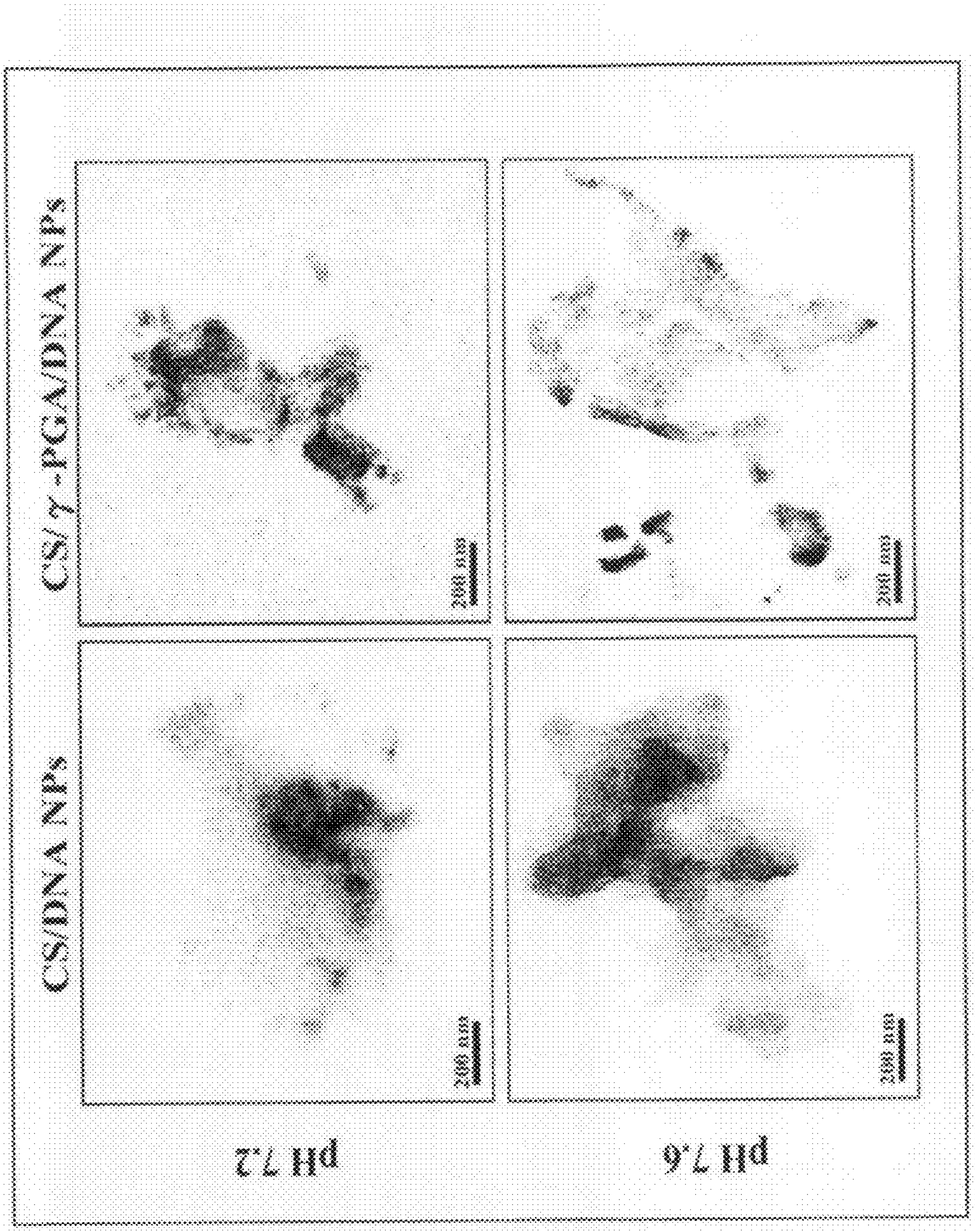
FIG. 11 shows TEM micrographs of CS/DNA NPs and CS/γ-PGA/DNA NPs at pH 7.2 and pH 7.6 (simulating the pH environments in the cytoplasm and nuclei of cells, respectively). CS: chitosan; γ-PGA: poly-γ-glutamic acid; NPs: nanoparticles.

At pH 7.2 and pH 7.6 (simulating the pH environments in the cytoplasm and nuclei of cells, respectively), most amino groups on CS are in the form of —$NH_2$. There is little electrostatic interaction between the deprotonated CS and DNA/γ-PGA. CS/DNA NPs and CS/γ-PGA/DNA NPs become unstable and subsequently break apart (FIG. 11). These results indicate that both CS/DNA and CS/γ-PGA/DNA NPs are pH-sensitive.

Animal Study with DNA-Loaded NPs

A carrier must release its encapsulated DNA at some point in the delivery process. The NPs prepared herein are pH-sensitive. At pH values simulating the environments of cytoplasm and nuclei within the cell, both CS/DNA NPs and CS/γ-PGA/DNA NPs become unstable and break apart in a short time (FIG. 11). Therefore, once into skin cells, both test NPs and control NPs might collapse, subsequently release the encapsulated DNA and facilitate expression of the encoded protein.

The Balb/C mice (female, 10-12 weeks old; n=5) were used in the study of DNA delivery. Mice were anesthetized using pentobarbital prior to experiment. After removing the hair covering the abdomen, the skin was wiped with an alcohol swab and allowed to air dry. Subsequently, control NPs (CS/DNA NPs) or test NPs (CS/γ-PGA/DNA NPs) containing 10 μg pEGFP-N2 in sterile DI water (5 μl) were loaded in a low-pressure gene gun and then bombarded into the skin. The helium pressure used was about 100 psi.

CLSM was used to visualize the penetration depth of the FITC-labeled NPs bombarded into the mouse skins using a low-pressure gene gun (about 50-150 psi). This non-invasive method allows for optical sectioning and imaging of the bombarded NPs in the mouse skins, without disrupting their structures. In fluorescence images after 3D reconstruction (not shown), both test NPs and control NPs are able to penetrate into the mouse skins after bombardment. The area of fluorescence signals observed for the group bombarded by CS/γ-PGA/DNA NPs is broader (the XY plane) and appears at a deeper level (the XZ plane) than that bombarded by CS/DNA NPs.

CS/DNA NPs were found in the superficial layer of epidermis (including the stratum corneum), whereas CS/γ-PGA/DNA NPs were able to penetrate into deeper regions in the epidermis. Also, there are more CS/γ-PGA/DNA NPs bombarded into the skin as compared with CS/DNA NPs. These observations could be attributed to the fact that CS/γ-PGA/DNA NPs are more compact in their internal structures (with a better integrity propensity; less propensity for breaking-up) and have a greater density than the density of their CS/DNA counterparts, thus having a larger momentum to penetrate into the skin barrier. Some aspects of the invention relate to a nanoparticle system that enhances penetrating efficiency overcoming the skin barrier when bombarded into the skin, wherein the nanoparticle system comprises a composition of CS, γ-PGA, and DNA.

The animal test results show more EGFP (enhanced green fluorescent protein) expression for CS/γ-PGA/DNA NPs than for CS/DNA NPs at 24 hours after bombardment (figures not shown)). EGFP expression was mainly localized to the suprabasal layers of epidermis for the group bombarded by CS/γ-PGA/DNA NPs. In contrast, for the group of CS/DNA NPs, EGFP expression was limited to the superficial layer of epidermis. Selective gene expression in the epidermis has potential advantages in gene therapies for various epidermal disorders.

Nanoparticles for Transdermal Bombardment Delivery

Nanoparticles composed of chitosan (CS) and polyglutamic acid, such as 7-polyglutamic acid (γPGA) or α-polyglutamic acid (αPGA), and a bioactive agent (such as DNA or siRNA) were prepared by ionotropic gelation to evaluate the topical application of CS-based nanoparticles containing pDNA as a potential approach to genetic immunization using a nanoparticle projectile bombardment gun or a conventional gene gun. In one embodiment, the obtained TEM micrographs showed that CS/VGA nanoparticles encapsulated with pDNA had a spherical (or spheroidal) morphology. In the animal study, CS/γ-PGA nanoparticles encapsulated with pDNA bombarded with a gene gun successfully penetrated the skin of a mouse model and EGFP was expressed. The results support that CS/PGA nanoparticles can substitute gold particles as a DNA carrier. The disadvantages of the conventional DNA coated gold particles via a gene gun approach include: (1) The DNA is coated on surface of a gold particle and the coated DNA may subject to attrition or reduced efficiency due to surface contact with other media during the delivery phase; (2) non-biodegradable gold particles; (3) lack of the ability of controlled release; and (4) high operating pressure using a conventional gene gun. On the contrary, the DNA or bioactive agent is encapsulated in nanoparticles of the present invention (as opposed to a conventional "coating" of DNA on surfaces of the gold particles) to preserve its efficacy, bioavailability, and biodurability with biodegradability of sustained release capability.

Nanoparticle Preparation for Targeted Epidermal Delivery

Nanoparticles encapsulated with pDNA (pEFGP-N2) were produced by ionotropic gelation (FIG. 1). Briefly, γPGA solution was mixed with pDNA and added into a CS solution in various $NH_3^+/COO^-$ ratios under gentle stirring at room temperature. The size and zeta potential of the prepared nanoparticles were measured using a Zetasizer (3000HS, Malvern Instruments Ltd., Worcestershire, UK). The encapsulation efficiency of the nanoparticles was analyzed. Furthermore, the morphology of the prepared nanoparticles was examined by transmission electron microscopy (TEM).

Some aspects of the invention relate to a pharmaceutical composition of nanoparticles for transdermal nucleic acid delivery, the nanoparticles comprising a first component of a positively charged chitosan and the nucleic acid, wherein the nucleic acid is encapsulated within the nanoparticles or electrostatically loaded on an exterior surface of the nanoparticles, the nanoparticles having a mean particle size between about 50 and 500 nanometers. In one embodiment, the nanoparticles further comprise a second component of negatively charged substrate in a core portion of the nanoparticles, the second component being complexed with the first component, wherein the second component comprises a material selected from the group consisting of γ-PGA, α-PGA, PGA derivatives, glycosaminoglycans, heparin, and small molecular weight heparin.

EXAMPLE NO. 12

Animal Feasibility Study of DNA-Loaded Nanoparticles

Balb/C mice (male, 10-12 weeks old) were used for the animal study. After removing the hair covering the abdomen, the skins were bombarded by selected nanoparticle (encapsulated with pDNA) solutions using a gene gun. After 24 hours, the mice were sacrificed and the skins were collected. EGFP expression was observed using an inversed confocal laser scanning microscope (CLSM, TCS SL, Leica, Germany). To measure the penetration depth of the nanoparticles, FITC-labeled nanoparticle solutions were loaded in the gene gun and bombarded. After 1 hour, the mice were sacrificed and the bombarded abdomen skins were collected and evaluated using CLSM.

After FITC-labeled CS nanoparticles were bombarded via a gene gun into the skin, they were clearly observed by CLSM at 40-80 μm depth into the skin. This indicated that the prepared nanoparticles are able to penetrate the skin of mice. Additionally, green fluorescence of EGFP was present in the skin layer of mice, after 24 hours of bombardment of the nanoparticles encapsulated with pDNA in the animal study.

Conventional Gene Gun

In general, "gene gun" is a device that delivers DNA-coated particles to cells by microprojectile bombardment with extremely high-speed delivery. In one example, the Helios® Gene Gun has been a new way for in vivo transformation of cells or organisms (i.e. gene therapy, genetic immunization, or DNA vaccination). This gun uses Biolistic® particle bombardment where DNA- or RNA-coated gold particles are loaded into the gun and one pulls the trigger for delivery. A high pressure helium pulse delivers the coated gold particles into virtually any target cell or tissue. The particles carry the DNA so that one does not have to remove cells from tissue in order to transform the cells. One model of the Helios gene gun system, 220-240 V, is used for biolistic particle delivery of biomaterials into cells. This handheld device employs an adjustable helium pulse to sweep DNA-, RNA-, and other biomaterial-coated gold microcarriers from the inner wall of a small plastic cartridge directly into target cells. This system has a 2 square-centimeter target area, and uses a pressure range of 100-600 psi. The system includes the Helios gene gun, helium hose assembly, helium regulator, tubing prep station, syringe kit, tubing cutter, and Helios gene gun optimization kit. Dimensions are 20×25 cm (manufactured by Bio-Rad, Hercules, Calif.). The gene gun is a device for injecting cells with genetic information, originally designed for plant transformation. The payload is an elemental particle of a heavy metal coated with plasmid DNA. The actual name of the gene gun is the Biolistic Particle Delivery System, and this technique is often simply referred to as "biolistics"—a cross between biology and ballistics.

In another example, a model of the gene gun consists of two small 6"×7"×10" stainless steel chambers connected to a 2 HP vacuum pump. When the technician flicks the switch on the outside of the second chamber, helium is released at up to 1000 psi. The blast ruptures a first disk about the size of a nickel. The explosion of the first disk releases a shock wave which travels 1 centimeter until it hits a second disk, which is free to move. Attached to the front of that second disk is microscopic tungsten or gold particles 1 micron in diameter coated with thousands of DNA molecules. This second disk travels another centimeter at the speed of a rifle bullet, for example about 1300 feet per second, and hits a screen, which detains the second disk, but launches the microscopic particles toward the target cells. The particles penetrate the cells and release the DNA, which is diffused into the nucleus and incorporated by the chromosomes of the plant. One common way of introducing DNA into plant cells is through DNA coated particles (e.g. one micron gold particles) that are literally shot through the cell wall. The gene gun was originally a nail gun for concrete surfaces that is modified to fire tungsten particles. Later the design was greatly refined. Improvements include the use of helium propellant and a multi-disk-collision delivery mechanism. Other heavy metals such as gold and silver are also used, but not as frequently due to reasons of availability and cost. The gene gun is very useful in applications such as transfection in agriculture, gene therapy or gene vaccine.

Another model of microprojectile bombardment gun is the "Cloning Gun™" that is a cordless, rechargeable, hand-held electroporation instrument. A cloning gun generally achieves transfection efficiencies exceeding 50% of viable cells with a variety of standard mammalian cell lines.

Nanoparticle Bombardment Gun for Transdermal Delivery

The nanoparticle bombardment gun ("NBG gun") may be modified from a conventional gene gun in that the NBG gun operates at a lower pressure of helium sources (in the range of less than 100 psi, preferably less than 90 psi, and most preferably between about 20 to 90 psi) for propelling the nanoparticles (in the range of about 50 to 500 nanometers, preferably in the range of 100 to 300 nanometers, and most preferably in the range of 150 to 250 nanometers) that are made of non-metallic material (preferably biodegradable material) instead of metals, such as gold, silver or tungsten. The nanoparticle bombardment gun uses neither a needle nor any sharp object to penetrate into the skin. Nevertheless, the nanoparticle exit-end of the NBG gun is usually placed against the skin for targeted epidermal delivery. In one embodiment, the NBG gun consists of a solenoid valve with NPT female fittings. On the input side, the solenoid is attached to a tubing that is connected to the helium regulator. On the other side, it is attached to a filter holder which acts as the support to load the nanoparticles to deliver. It then fits tightly into the O-ring fitting. The solenoid is wired to a trigger that consists of a momentary switch, which fires a one-shot relay switch. The 120V AC current powers both the relay and the solenoid.

An advantage of administering a protein or peptide via a biodegradable nanoparticle capable of producing an immune response is the ability to cause the immunogen to be effectively presented to the animal or human over an extended period of time. Similarly, an advantage of administering siRNA via a biodegradable nanoparticle is the ability for siRNA to interfere with the expression of a specific gene over an extended period of time or in a control-release manner. RNA silencing, the process triggered by siRNA molecules, can turn off the ability of cancer cells to produce the key proteins that make them different from normal cells, and by doing so, stop malignancy in its tracks. As used herein, the term "tissue cells" means cells residing in a tissue whereas the term "tissue" means an aggregation of similarly specialized cells united in the performance of a particular function. Animal tissue cells can be bombarded in situ and the tissue is transformed in situ in the animal in which it is to be maintained. In general, the polynucleic acid sequence carried by the biodegradable nano-projectile of the present invention is a recombinant construct of a gene and a regulatory element. The construct may take any suitable form, such as plasmid, a genomic viral DNA sequence, such as a bovine papillomavirus vector (see E. Chen et al., 299 *Nature* 529, 1982), a retroviral RNA sequence, derivatives of the foregoing, and synthetic oligonucleotides. One aspect of the invention provides a biodegradable nanoparticle of the present invention as the nano-projectile used in nano-projectile bombardment in animals for administering a bioactive agent.

Some aspects of the invention provide a pharmaceutical composition of nanoparticles for transdermally lodging in a target tissue of an animal subject, each nanoparticle comprising a first component of a positively charged chitosan, a second component of negatively charged substrate that complexes with the first positively charged component, and at least one bioactive agent encapsulated within the nanoparticles. In one embodiment, the nanoparticles are biodegradable. In another embodiment, the nanoparticle is about 50 nm to 500 nm in size.

The regulatory sequence is positioned in the polynucleic acid sequence in operative association with the gene so as to be capable of inducing transcription of the gene. Regulatory sequences which may be used to provide transcriptional control of the gene in the polynucleic acid sequence are generally promoters which are operable in the target tissue cells. Other regulatory elements which may optionally be incorporated into the polynucleic acid sequence include enhancers, promoters, termination sequences, and polyadenylation sites, as known in the art, as necessary to obtain the desired degree of expression of the gene in the cell into which it is inserted.

By ways of examples, genes that code for proteins or peptides which produce an endocrine response are genes that code for Factor VIII, genes that code for plasminogen activators such as tissue plasminogen activator (TPA) and urokinase, genes that code for growth hormones such as human or bovine growth hormone, genes that code for insulin, and genes that code for releasing factors such as Luteinizing Hormone Releasing Hormone. An endocrine response is a physiological response in the animal at a point sufficiently removed from the transformed tissue region to require that the protein or peptide travel through the circulatory or lymphatic system of the subject.

Skin in an animal is formed from an outer epidermis, an underlying dermis, and a hypodermis. The dermis and/or the hypodermis are the preferred tissue targets when the object of the transformation is to administer a protein or peptide to the animal in a manner which will evoke a physiological response thereto in the animal.

Some aspects of the invention relate to a method of administering a bioactive agent into tissue cells transcutaneously or transdermally in an animal subject by in situ nano-projectile bombardment, comprising: (a) selecting a target skin tissue of the animal subject, wherein the target skin tissue is selected from the group consisting of epidermis tissue, dermis tissue, and hypodermis tissue; (b) providing nano-projectiles, wherein the bioactive agent is encapsulated in the nano-projectiles, each nano-projectile being in a nanoparticle form; and (c) accelerating the nano-projectiles at the animal subject so that the nano-projectiles contact the animal's epidermis at a speed sufficient to penetrate the epidermis and lodge in the target skin tissue. In one embodiment, the speed in the accelerating step is generated by a pressure source for firing a nano-projectile bombardment gun at less than about 90 psi (say, between about 20 and about 90 psi). In one embodiment, the nanoparticles or nano-projectiles of the present invention are freeze-dried nanoparticles. In another embodiment, the penetration depth and gene expression of the transdermal DNA or siRNA delivery is improved or enhanced using a low-pressure bombardment gene gun (preferably between about 20 and 90 psi).

One aspect of the invention provides a method of administering a bioactive agent into tissue cells transcutaneously or transdermally in an animal subject by in situ nano-projectile bombardment, wherein the nano-projectiles are biodegradable. In one embodiment, the nano-projectiles are made of biodegradable material selected from the group consisting of poly(L-lactic acid), polyglycolic acid, poly (D,L-lactide-co-glycolide), poly (ester amides), polycaprolactone, and co-polymers thereof.

One aspect of the invention provides a method of administering a bioactive agent into tissue cells transcutaneously or transdermally in an animal subject by in situ nano-projectile bombardment, wherein the nano-projectile comprises a positively charged shell substrate and a negatively charged core substrate. In one embodiment, the shell substrate comprises a material selected from the group consisting of chitosan, low molecular weight chitosan, chitin, chitosan oligosaccharides, and chitosan derivatives thereof. In another embodiment, the low molecular weight chitosan is characterized with an effective solubility in water at a pH range of between about 5.0 to 6.5, preferably about 6.0 to 6.2. The effective solubility may be defined as more than 50% of the raw chitosan is dissolved within about 10 minutes under vigorous stirring.

One aspect of the invention provides a method of administering a bioactive agent into tissue cells transcutaneously or transdermally in an animal subject by in situ nano-projectile bombardment, wherein the core substrate comprises a material selected from the group consisting of γ-PGA, α-PGA, PGA derivatives, heparin, heparin analogs, low molecular weight heparin, glycosaminoglycans, and alginate, wherein the core substrate may be characterized to complex with the shell substrate or with the encapsulated bioactive agent.

One aspect of the invention provides a method of administering a bioactive agent into tissue cells transcutaneously or transdermally in an animal subject by in situ nano-projectile bombardment, wherein the nano-projectile is about 50 μm to 500 μm in size, preferably about 100 μm to 300 μm in size, and most preferably about 150 μm to 250 μm in size.

One aspect of the invention provides a method of administering a bioactive agent transcutaneously or transdermally in an animal subject by in situ nano-projectile bombardment, wherein the bioactive agent is a protein, a peptide, plasmid protein, or insulin. In one embodiment, the molecular formula of the insulin is selected from the group consisting of $C_{254}H_{377}N_{65}O_{75}S_6$, $C_{257}H_{383}N_{65}O_{77}S_6$, $C_{256}H_{381}N_{65}O_{79}S_6$, and $C_{267}H_{404}N_{72}O_{78}S_6$.

One aspect of the invention provides a method of administering a bioactive agent transcutaneously or transdermally in an animal subject by in situ nano-projectile bombardment, wherein the bioactive agent is selected from the group consisting of chondroitin sulfate, hyaluronic acid, calcitonin, vancomycin, and a growth factor. In one embodiment, the growth factor is selected from the group consisting of Vascular Endothelial Growth Factor (VEGF), basic Fibroblast Growth Factor (bFGF), Platelet Derived Growth Factor (PDGF), Platelet Derived Angiogenesis Factor (PDAF), Transforming Growth Factor-β (TGF-β), Transforming Growth Factor-α (TGF-α), Platelet Derived Epidermal Growth Factor (PDEGF), Platelet Derived Wound Healing Formula (PDWHF), epidermal growth factor, insulin-like growth factor, acidic Fibroblast Growth Factor (aFGF), and combinations thereof.

Some aspects of the invention provide a process of administering nanoparticles having the pharmaceutical composition of the present invention into the animal subject, wherein the process comprises a transdermal step so that the nanoparticles lodge in the target tissue of the animal subject. In a preferred embodiment, the transdermal step of the process comprises an in situ nano-projectile bombardment, the bombardment comprising: (a) providing the nanoparticles as nano-projectiles; (b) loading the nano-projectiles in a nano-projectile pressurized gun; and (c) accelerating the nano-projectiles at a target skin of the animal subject so that the nano-projectiles contact an animal's epidermis at a speed sufficient to penetrate the epidermis and lodge in the target tissue.

Freeze-Dried Nanoparticles

A pharmaceutical composition of nanoparticles of the present invention may comprise a first component of at least one bioactive agent, a second component of chitosan (including regular molecular weight and low molecular weight chitosan), and a third component that is negatively charged. In one embodiment, the second component dominates on a surface of the nanoparticle. In another embodiment, the low molecular weight chitosan has a molecular weight lower than that of a regular molecular weight chitosan. The nanoparticle may further comprise tripolyphosphate and magnesium. For example, a first solution of (2 ml 0.1% γ-PGA aqueous solution @pH 7.4+0.05% Insulin+0.1% Tripolyphosphate (TPP)+0.2% MgSO4) is added to a base solution (10 ml 0.12% chitosan aqueous solution @pH 6.0) as illustrated in Example no. 4 under magnetic stirring at room temperature. Nanoparticles were collected by ultracentrifugation at 38,000 rpm for 1 hour. Supernatants were discarded and nanoparticles were resuspended in deionized water for freeze-drying preparation. Other operating conditions or other bioactive agent (such as protein, peptide, siRNA, growth factor, the one defined and disclosed herein, and the like) may also apply.

Several conventional coating compounds that form a protective layer on particles are used to physically coat the nanoparticles before a freeze-drying process. The coating compounds may include trehalose, mannitol, glycerol, and the like. Trehalose, also known as mycose, is an alpha-linked (disaccharide) sugar found extensively but not abundantly in nature. It can be synthesized by fungi, plants and invertebrate animals. It is implicated in anhydrobiosis—the ability of plants and animals to withstand prolonged periods of desiccation. The sugar is thought to form a gel phase as cells dehydrate, which prevents disruption of internal cell organelles by effectively splinting them in position. Rehydration then allows normal cellular activity to resume without the major, generally lethal damage, which would normally follow a dehydration/rehydration cycle. Trehalose has the added advantage of being an antioxidant.

Trehaloze has a chemical formula as $C_{12}H_{22}O_{11}.2H_2O$. It is listed as CAS no. 99-20-7 and PubChem 7427. The molecular structure for trehalose is shown below.

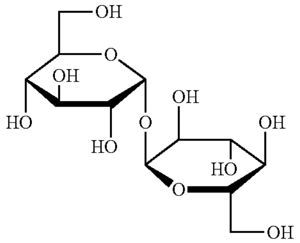

Trehalose was first isolated from ergot of rye. Trehalose is a non-reducing sugar formed from two glucose units joined by a 1-1 alpha bond giving it the name of α-D-glucopyranosyl-(1→1)-α-D-glucopyranoside. The bonding makes trehalose very resistant to acid hydrolysis, and therefore stable in solution at high temperatures even under acidic conditions. The bonding also keeps non-reducing sugars in closed-ring form, such that the aldehyde or ketone end-groups do not bind to the lysine or arginine residues of proteins (a process called glycation). Trehalose has about 45% the sweetness of sucrose. Trehalose is less soluble than sucrose, except at high temperatures (>80° C.). Trehalose forms a rhomboid crystal as the dihydrate, and has 90% of the calorific content of sucrose in that form. Anhydrous forms of trehalose readily regain moisture to form the dihydrate. Trehalose has also been used in at least one biopharmaceutical formulation, the monoclonal antibody trastuzumab, marketed as Herceptin. It has a solubility of 68.9 g/100 g $H_2O$ at 20° C.

Mannitol or hexan-1,2,3,4,5,6-hexyl ($C_6H_8(OH)_6$) is an osmotic diuretic agent and a weak renal vasodilator. Chemically, mannitol is a sugar alcohol, or a polyol; it is similar to xylitol or sorbitol. However, mannitol has a tendency to lose a hydrogen ion in aqueous solutions, which causes the solution to become acidic. For this, it is not uncommon to add a substance to adjust its pH, such as sodium bicarbonate. Mannitol has a chemical formula as $C_6H_{14}O_6$. It is listed as CAS no. 69-65-8 and PubChem 453. The molecular structure for mannitol is shown below.

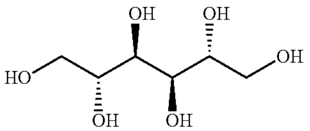

Glycerol is a chemical compound with the formula $HOCH_2CH(OH)CH_2OH$. This colorless, odorless, viscous liquid is widely used in pharmaceutical formulations. Also commonly called glycerin or glycerine, it is a sugar alcohol and fittingly is sweet-tasting and of low toxicity. Glycerol has three hydrophilic alcoholic hydroxyl groups that are responsible for its solubility in water and its hygroscopic nature. Glycerol has a chemical formula as $C_3H_5(OH)_3$. It is listed as CAS no. 56-81-5. The molecular structure for glycerol is shown below.

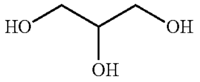

EXAMPLE NO. 13

Freeze-Drying Process for Nanoparticles

Nanoparticles (at 2.5% concentration) were mixed with solution from four types of liquid at a 1:1 volume ratio for about 30 minutes until fully dispersed. The mixed particle-liquid was then freeze-dried under a lyophilization condition, for example, at −80° C. and <25 mmHg pressure for about 6 hours. The four types of liquid used in the experiment include: (A) DI water; (B) trehalose; (C) mannitol; and (D) glycerol, whereas the concentration of the liquid (A) to liquid (C) in the solution was set at 2.5%, 5% and/or 10%. After a freeze-drying process, the mixed particle-liquid was rehydrated with DI water at a 1:5 volume ratio to assess the integrity of nanoparticles in each type of liquid. The results are shown in Table 6. By comparing the particle size, polydispersity index and zeta-potential data, only the nanoparticles from the freeze-dried particle-trehalose runs (at 2.5%, 5%, and 10% concentration level) show comparable properties as compared to those of the before-lyophilization nanoparticles. Under the same data analysis, the nanoparticles from the freeze-dried particle-mannitol runs (at 2.5%, and 5% concentration level) show somewhat comparable properties as compared to those of the pre-lyophilization nanoparticles.

TABLE 6

Properties of nanoparticles before and after an exemplary freeze-drying process.

| | (before a freeze-drying process) NPs solution |
|---|---|
| Conc. | 2.50% |
| Size (mm) | 266 |
| Kcps | 352.2 |
| PI | 0.291 |
| Zeta Potential | 25.3 |

(after a freeze-drying process)

| | A: DI Water DI water + NPs (volume 1:1) | B: Trehalose Trehalose + NPs (volume 1:1) | | | C: Mannitol Mannitol + NPs (volume 1:1) | | D: Glycerol Glycerol + NPs (volume 1:1) | | |
|---|---|---|---|---|---|---|---|---|---|
| Conc. | | 2.50% | 5.00% | 10.00% | 2.50% | 5.00% | 2.50% | 5.00% | 10.00% |
| Size (mm) | 9229.1 | 302.4 | 316.7 | 318.9 | 420.1 | 487.5 | 6449.1 | 7790.3 | 1310.5 |

TABLE 6-continued

| Properties of nanoparticles before and after an exemplary freeze-drying process. | | | | | | | | | |
|---|---|---|---|---|---|---|---|---|---|
| Kcps | 465.3 | 363.7 | 327.7 | 352.2 | 305.4 | 303.7 | 796.1 | 356.1 | 493.3 |
| PI | 1 | 0.361 | 0.311 | 0.266 | 0.467 | 0.651 | 1 | 1 | 1 |
| Zeta Potential | | 25.6 | 24.6 | 24.7 | 24.4 | 25.3 | | | |

Nanoparticle Loaded with siRNA Compound

One aspect of the invention provides a method of administering a bioactive agent transcutaneously or transdermally into tissue cells in an animal subject by in situ nano-projectile bombardment of the present invention, wherein the bioactive agent is RNA or siRNA. Ribonucleic acid (RNA) is a nucleic acid polymer consisting of nucleotide monomers that plays several important roles in the processes that translate genetic information from deoxyribonucleic acid (DNA) into protein products. RNA acts as a messenger between DNA and the protein synthesis complexes known as ribosomes, forms vital portions of ribosomes, and acts as an essential carrier molecule for amino acids to be used in protein synthesis. RNA is very similar to DNA, but differs in a few important structural details. RNA nucleotides contain ribose sugars while DNA contains deoxyribose and RNA uses predominantly uracil instead of thymine present in DNA. RNA is transcribed from DNA by enzymes called RNA polymerases and further processed by other enzymes. RNA serves as the template for translation of genes into proteins, transferring amino acids to the ribosome to form proteins, and translating the transcript into proteins.

Figure 8:
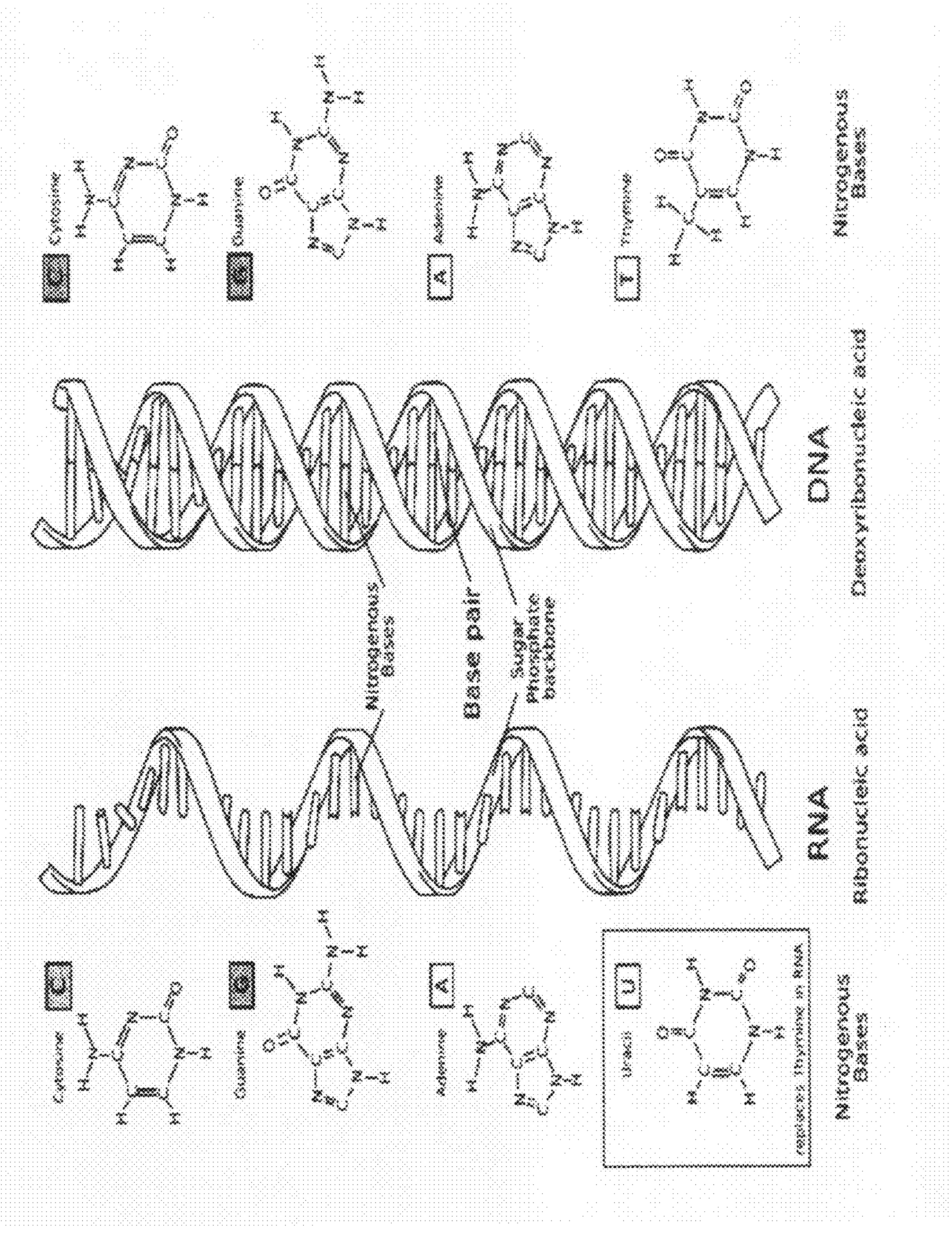
FIG. 8 shows chemical and stereochemical structures for a representative RNA and DNA.

RNA is a polymer with a ribose and phosphate backbone and four different nucleotide bases: adenine, guanine, cytosine, and uracil. The first three are the same as those found in DNA, but in RNA thymine is replaced by uracil as the base complementary to adenine. This base is also a pyrimidine and is very similar to thymine. In DNA, however, uracil is readily produced by chemical degradation of cytosine, so having thymine as the normal base makes detection and repair of such incipient mutations more efficient. Thus, uracil is appropriate for RNA, where quantity is important but lifespan is not, whereas thymine is appropriate for DNA where maintaining sequence with high fidelity is more critical. FIG. 8 show chemical and stereochemical structures for a representative DNA and RNA (Wikimedia Commons).

There are also numerous modified bases and sugars found in RNA that serve many different roles. Pseudouridine (T), in which the linkage between uracil and ribose is changed from a C—N bond to a C—C bond, and ribothymidine (Ψ), are found in various places (most notably in the TΨC loop of tRNA). Another notable modified base is hypoxanthine (a delaminated Guanine base whose nucleoside is called Inosine). Inosine plays a key role in the Wobble Hypothesis of the Genetic Code. There are nearly 100 other naturally occurring modified nucleosides, of which pseudouridine and nucleosides with 2'-O-methylribose are by far the most common. The specific roles of many of these modifications in RNA are not fully understood. However, it is notable that in ribosomal RNA, many of the post-translational modifications occur in highly functional regions, such as the peptidyl transferase center and the subunit interface, implying that they are important for normal function.

The most important structural feature of RNA, that distinguishes it from DNA is the presence of a hydroxyl group at the 2'-position of the ribose sugar. The presence of this functional group enforces the C3'-endo sugar conformation (as opposed to the C2'-endo conformation of the deoxyribose sugar in DNA) that causes the helix to adopt the A-form geometry rather than the B-form most commonly observed in DNA. This results in a very deep and narrow major groove and a shallow and wide minor groove. A second consequence of the presence of the 2'-hydroxyl group is that in conformationally flexible regions of an RNA molecule (that is, not involved in formation of a double helix), it can chemically attack the adjacent phosphodiester bond to cleave the backbone.

Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome; the complexity of these pathways is only now being elucidated.

SiRNAs were first discovered by David Baulcombe's group in Norwich, England, as part of post-transcriptional gene silencing (PTGS) in plants, and published their findings in Science in a paper titled "A species of small antisense RNA in posttranscriptional gene silencing in plants". Shortly thereafter, in 2001, synthetic siRNAs were then shown to be able to induce RNAi in mammalian cells by Thomas Tuschl and colleagues in a paper published in *Nature*. This discovery led to a surge in interest in harnessing RNAi for biomedical research and drug development.

SiRNAs have a well-defined structure: a short (usually 21-nt) double-strand of RNA (dsRNA) with 2-nt 3' overhangs on either end:

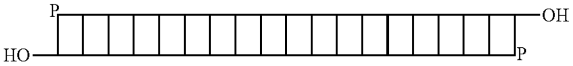

Schematic representation of a siRNA molecule: a ~19-21basepair RNA core duplex that is followed by a 2 nucleotide 3′ overhang on each strand. OH: 3′ hydroxyt, P: 5′ phosphate.

Each strand has a 5' phosphate group and a 3' hydroxyl (—OH) group. This structure is the result of processing by dicer, an enzyme that converts either long dsRNAs or small hairpin RNAs into siRNAs. SiRNAs can also be exogenously (artificially) introduced into cells by various transfection methods to bring about the specific knockdown of a gene of interest. Essentially any gene of which the sequence is known can thus be targeted based on sequence complementarity with an appropriately tailored siRNA. This has made siRNAs an important tool for gene function and drug target validation studies in the post-genomic era.

RNA interference (RNAi) is a phenomenon in which the introduction of double-stranded RNA (dsRNA) into a diverse range of organisms and cell types causes degradation of the complementary mRNA. Upon introduction into the cell, long dsRNAs enter a cellular pathway that is commonly referred to as the RNA interference pathway. First, the dsRNA's are cleaved into short 21-25 nucleotide small interfering RNAs, or siRNAs, by a ribonuclease known as Dicer. The siRNAs subsequently assemble with protein components into an RNA-induced silencing complex (RISC). The siRNA strands are then unwound to form activated RISCs. These activated RISCs then bind to complementary RNA molecules by base pairing interactions between the siRNA antisense strand and the mRNA. The bound mRNA is cleaved and sequence specific degradation of mRNA results in gene silencing. Although there are different methods to generate siRNA for gene silencing, the easiest and most efficient way to achieve RNAi is to use synthetic small-interfering RNA (siRNA).

In an exemplary illustration, RNA silencing, the process triggered by siRNA molecules, can turn off the ability of cancer cells to produce the key proteins that make them different from normal cells, and by doing so, stop malignancy in its tracks. Early proof-of-principle experiments in various tumor cells showed quickly that RNA silencing had great potential as a means for treating cancer.

RNA oligos are susceptible to degradation by exogenous ribonucleases introduced during handling. RNase-free reagents and supplies should be used. Oligonucleotides may be re-suspended at a convenient concentration in RNase-free sterile water. The use of DEPC-treated water is not recommended. DEPC-treated water is deionized diethylpyrocarbonate treated and 0.22 μm membrane-filtered. Dried RNA oligos are usually stable for 1 year at −20° C. Once re-suspended, oligonucleotides solutions are best kept frozen at −20° C. for several weeks and may remain stable for several months. The most important factor in storing working solutions is using nuclease-free, sterile water. Drying down of your oligos and keeping them at −20° C. is recommended for long-term storage. Some aspects of the invention relate to a siRNA-containing nanoparticle that has been lyophilized (for example, using a freeze dryer by Eyela Co. Ltd, Tokyo, Japan) and stored at −20° C. until it is ready for administering into the tissue cells transcutaneously or transdermally via the in situ nano-projectile bombardment method.

The function of a gene can be determined on the basis of the behavior of cells in which the level of gene expression or level of activity of the gene product has been reduced. Experimental procedures can be used to specifically inactivate or silence a target gene or inhibit the activity of its gene product. Inhibition of protein activity can be brought about at the level of gene transcription, protein translation or post translational modifications. For instance, the activity of a protein can be inhibited by directly inhibiting the activity of the protein such as altering a catalytic domain or alternatively by reducing the amount of the protein in the cell by reducing the amount of mRNA encoding the protein. In each case, the level of protein activity in the cell is reduced. Various techniques can be used to knock down the activity of a protein and these include knockout technologies (antibodies, antisense RNA, and RNA interference) and compounds that specifically inhibit the protein activity.

The ability to specifically knock down expression of a target gene by siRNA has many benefits. For example, siRNA could be used to mimic true genetic knockout animals to study gene function. There have been reports of using siRNA for various purposes including the inhibition of luciferase gene expression in human cells.

The in situ nano-projectile bombardment of the present invention discloses a method of administering a nanoparticle into cells transcutaneously or transdermally in an animal subject, the nanoparticle comprising potent and stable siRNA compounds (or siRNA-containing compounds) to silence the genes that causes serious diseases. The potent and stable siRNA compound may comprise a polynucleotide or vector for expressing short interfering RNAs (siRNAs) to inhibit the expression of a target gene. One aspect of the invention relates to delivering polynucleotides encoding polypeptides to vertebrate cells in vivo, preferably via a low pressure nano-projectile bombardment route. The siRNA compound may include a composition comprising the siRNA of interest and a pharmaceutically acceptable carrier or diluent. The ability to inhibit or disrupt the function of a specific gene is highly desirable. The ability to modulate the expression of a mutated allele or of an inappropriately expressed wild type allele in various diseases or disorders may therefore be used to provide therapies to treat the disorders.

The nanoparticles of the present invention may further comprise an adenovirus vector, wherein the adenovirus vector comprises a polynucleotide construct that may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell. In an alternate embodiment, the nanoparticles of the present invention may further comprise an adenovirus vector, wherein the adenovirus vector comprises a siRNA.

Multifunctional Nanoparticles for Transdermal DNA Delivery

Some aspects of the invention relate to biodegradable poly (lactic-co-glycolic acid) (PLGA) nanoparticles encapsulated with CdSe/ZnS quantum dots (QDs). The nanoparticles were prepared by an emulsion-solvent evaporation technique and cationically modified for DNA delivery by using polyvinyl alcohol (PVA)-glycol chitosan (gCS) blend as stabilizer and coating materials. The zeta potential of nanoparticle decreased with an increase in pH values and reached at about +6 in pH 7.4 PBS buffer. The obtained TEM micrographs showed that PLGA nanoparticles had a spherical morphology and shelled with gCS. To evaluate the feasibility of using a novel air injector for transdermal delivery of DNA by a topical application, gCS-coated nanoparticles were loaded with plasmid DNA as a potential carrier for genetic immunization using an air injector. In the study, the plasmid pEGFP-N2 was loaded on the surface of nanoparticles by electrostatic interaction between phosphate group of DNA and the amino group of gCS on the surface. In the animal study, an animal subject was bombarded by nanoparticles loaded with pEGFP-N2 with a gene gun. The nanoparticles successfully penetrated the skin of a mouse model and EGFP was expressed. The results revealed that gCS-coated nanoparticles may be used as a DNA carrier for transdermal DNA delivery via an air injector.

Some aspects of the invention relate to a unique form of needle-free gene delivery. The principle of the concept has been to accelerate DNA-coated gold particles to form sufficient momentum and kinetic energy to penetrate the skin barrier, stratum corneum, and express foreign proteins in the skin for a pharmacological effect or an immunological application. The antigen presenting cells (APCs) widely populated in the human skin, including Langerhans cells (LCs) in the epidermis and dendrite cells in the dermis, played a critically important role to the immune system. Numerous studies have been reported that direct targeting Langerhans cells in the epidermis can elicit humoral and cytotoxic T lymphocyte response by using a gene gun (*Vaccine* 1995; 13:1427-1430). One object of the present invention is to provide novel biodegradable nanoparticles for transdermally and painlessly delivering gene into skin and tracking the migration of LCs to the lymph nodes simultaneously. The topical application of biodegradable nanoparticles containing plasmid DNA as a potential means for gene-loaded immunization was evaluated using an air injector.

Some aspects of the invention relate to a pharmaceutical composition of nanoparticles for transdermal nucleic acid delivery, the nanoparticles comprising a first component of a positively charged chitosan, the nucleic acid being encapsulated within the nanoparticles or electrostatically loaded on an exterior surface of the nanoparticles, and at least one quantum dot in a core portion. In one embodiment, the quantum dot is a CdSe/ZnS quantum dot.

Biodegradable polymeric nanoparticles (NPs) have been widely investigated as a vehicle for gene delivery because of their good biocompatibility. In the study, we developed multifunctional nanoparticles for DNA delivery and tracking simultaneously. Biodegradable poly(lactic-co-glycolic acid) (PLGA) nanoparticles encapsulated with CdSe/ZnS quantum dots (QDs) were prepared by an emulsion-solvent evaporation technique and cationically modified for DNA delivery by using polyvinyl alcohol (PVA)-glycol chitosan (gCS) blend as stabilizer and coating materials.

EXAMPLE NO. 14

Nanoparticles Preparation Transdermal Delivery

Poly(D,L-lactic-co-glycolic acid) (75/25) (PLGA, inherent viscosity 0.16-0.29 dl/g) was obtained from Bio Invigor Co. (Taipei, Taiwan). Polyvinyl alcohol (PVA), glycol chitosan and dichloromethane (DCM) were bought from Sigma-Aldrich (St. Louis, Mo., USA). CdSe/ZnS quantum dots (QD) were purchased from Evident Technologies Inc. (Troy, N.Y., USA). The quantum dots, also known as nanocrystals, are a special class of materials known as semiconductors, which are crystals composed of periodic groups of II-VI, III-V, or IV-VI materials. Quantum dots are in a unique class of semiconductor because they are so small, ranging from 2-10 nanometers (10-50 atoms) in diameter, whose excitons are confined in all three spatial dimensions. As a result, they have properties that are between those of bulk semiconductors and those of discrete molecules. The use of quantum dots for highly sensitive cellular imaging has seen major advances over the past decade. The improved photostability of quantum dots for example, allows the acquisition of many consecutive focal-plane images that can be reconstructed into a high-resolution three-dimensional image. Another application that takes advantage of the extraordinary photostability of quantum dot probes is the real-time tracking of molecules and cells over extended periods of time. The quantum dots may be functionalized with tumor specific binding sites to specifically bind to tumor cells. Quantum dots with a stable polymer coating have been found to be essentially nontoxic. In one embodiment, the polyvinyl alcohol-glycol chitosan blend serves as a stable polymer that coats on a quantum dot.

Figure 12:
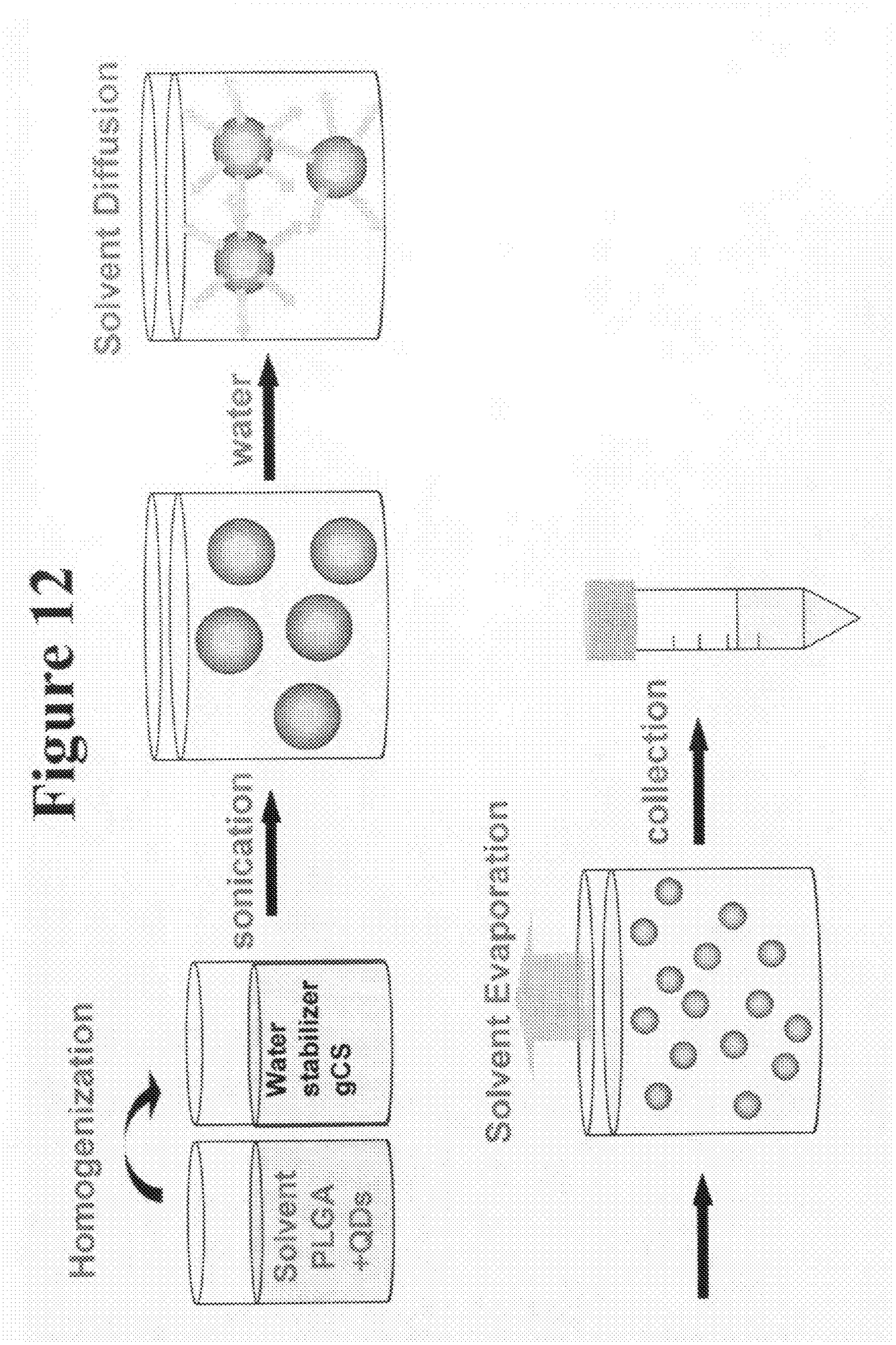
FIG. 12 shows an emulsion-solvent evaporation technique for PLGA/QD nanoparticles manufacturing.

The PLGA/QDs nanoparticles were prepared by emulsion-solvent evaporation technique with some modification (FIG. 12). PLGA (10 mg/ml) and QDs (1 mg/ml) were dissolved in dichloromethane. The 3 ml organic mixture with magnetite nanoparticles was added into 6 ml of an aqueous phase containing stabilizer (1 wt. % of PVA and 0.2 wt. % of glycol-chitosan) and emulsified with a high speed homogenizer (Polytron® PT 1200 E, Kinematica AG Lucerne, Switzerland) followed by sonication (Tapered Microtip 5 mm, Sonics & Materials, Newtown, Conn., USA). The emulsion was then transferred into 100 ml deionized water and allowed to stir uncovered overnight at room temperature in a fume hood to evaporate organic solvent. Nanoparticles were collected by centrifugation (60 min, 9000 rpm), washed three times and then were resuspended with deionized water.

Figure 13:
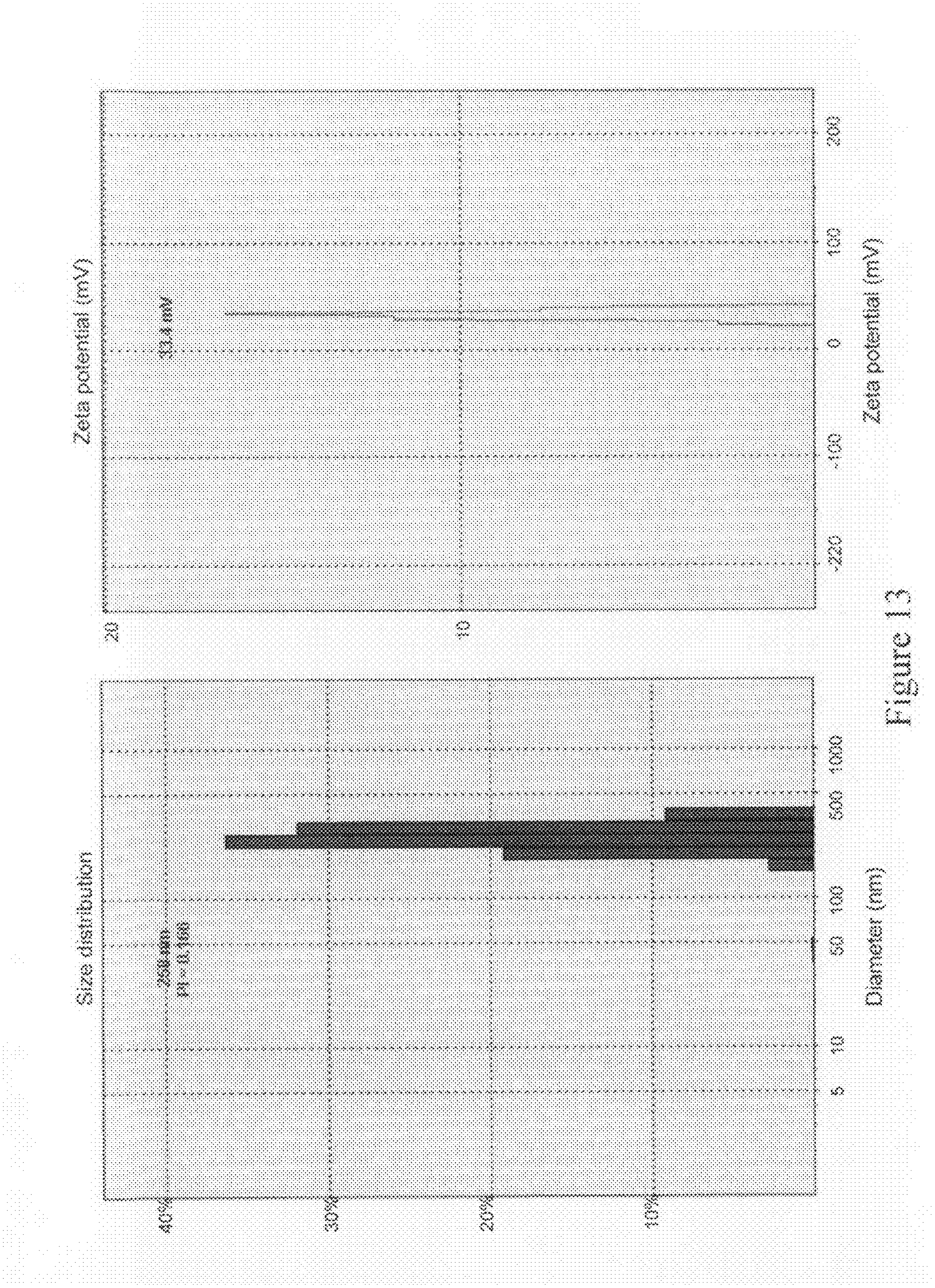
FIG. 13 shows the particle size and zeta potential of the PLGA/QD nanoparticles.

The morphology of the prepared NPs was examined by TEM (JEOL, Tokyo, Japan). The TEM sample was prepared by placing a drop of the NP suspension onto a 400 mesh copper grid coated with carbon. About 2 min after deposition, the grid was tapped with a filter paper to remove surface water and then stained using Osmium tetroxide. The size distribution and zeta potential of the prepared NPs were measured using DLS (Zetasizer, 3000 HS, Malvern Instruments Ltd., Worcestershire, UK) and shown in FIG. 13. Fluorescence properties of the nanoparticles were investigated by fluorescence spectrometry and the XRD patterns were recorded using CuKa radiation.

Figure 14:
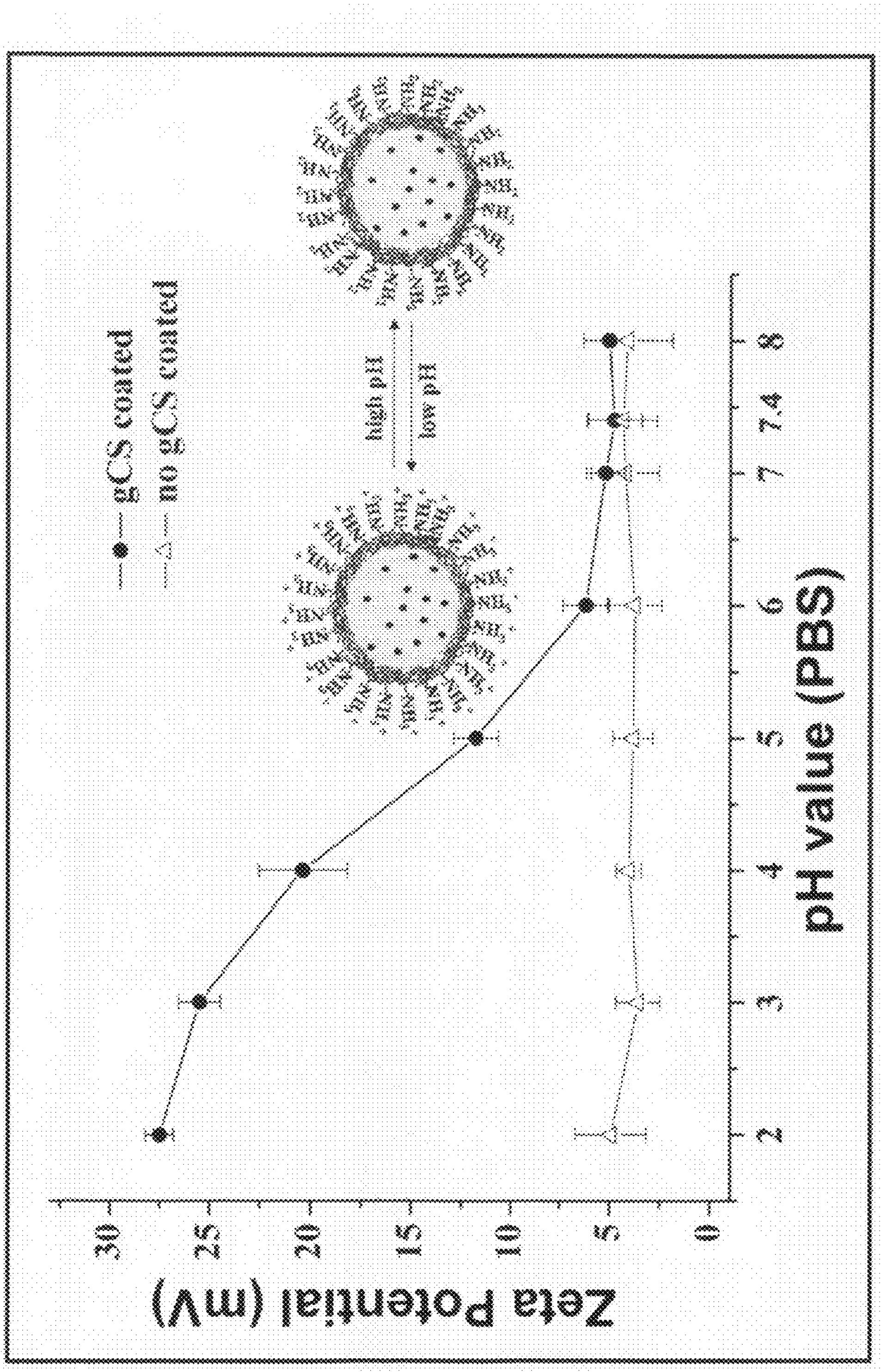
FIG. 14 shows the zeta potential versus pH values for gCS coated nanoparticles and control (i.e. no gCS coated).
Figure 15:
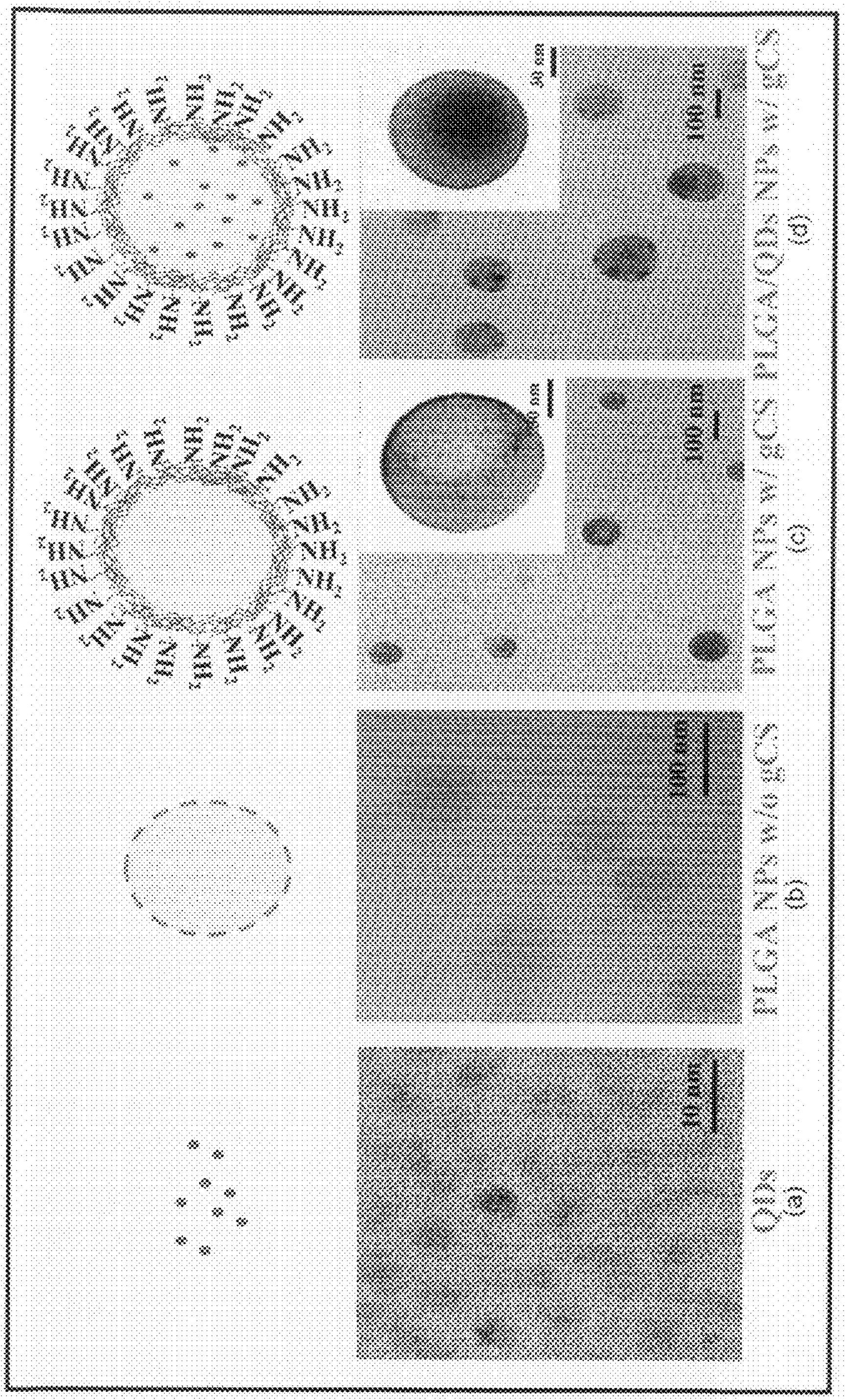
FIG. 15 shows TEM micrographs, indicating that PLGA/QD nanoparticles had a spherical morphology and shelled with gCS.

The QDs could be encapsulated in the core portion of the nanoparticles and the emission of the QDs do not change in the fluorescence spectra. The zeta potential of nanoparticles decreases with an increase in pH values and reached to +6 in pH 7.4 PBS buffer (FIG. 14), which is evident that gCS was coated on the surface of the nanoparticles. The obtained TEM micrographs show that the PLGA nanoparticles have a spherical morphology and shelled with gCS, which could further support the core-shell structure of the nanoparticles (FIG. 15). One aspect of the invention provides a core-shell structure of PLGA/QD NP with gCS (as shown in FIG. 15(*d*)) for multifunctional DNA delivery and real-time DNA tracking.

Some aspects of the invention relate to a pharmaceutical composition of nanoparticles for transdermal nucleic acid delivery, the nanoparticles comprising (a) a first component of a positively charged chitosan, (b) the nucleic acid being encapsulated within the nanoparticles or electrostatically loaded on an exterior surface of the nanoparticles, (c) at least one quantum dot in a core portion, and (d) PLGA substrate in the core portion, wherein the at least one quantum dot is dispersed within the PLGA substrate.

Figure 16:
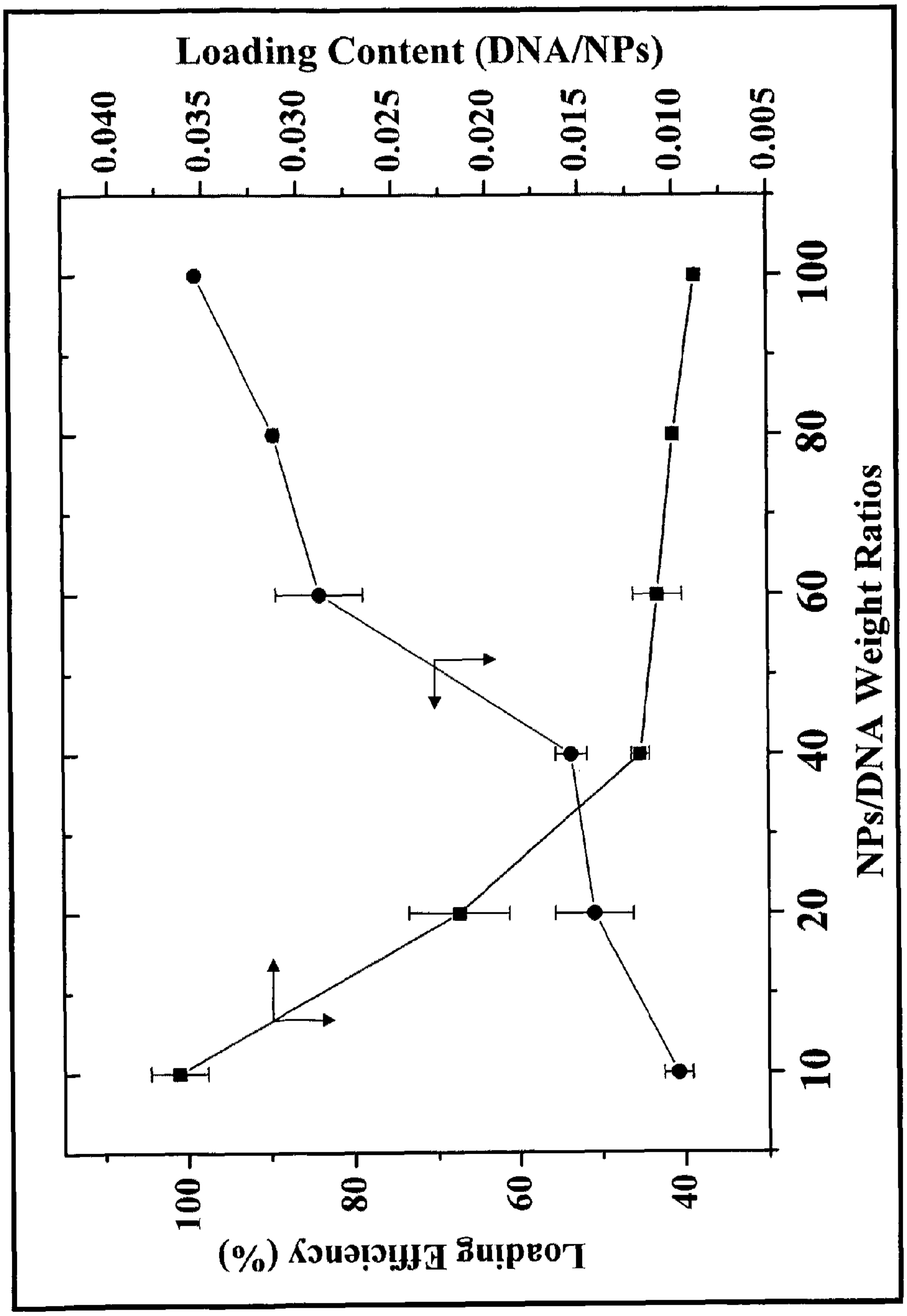
FIG. 16 shows the loading efficiency and loading content of DNA-loaded nanoparticles.

To evaluate the topical application of nanoparticles for transdermal delivery of DNA, nanoparticles were loaded with plasmid DNA. Reported plasmid pEGFP-N2 was loaded on the surface of nanoparticles by electrostatic interaction between phosphate group of DNA and the amino group of gCS on the surface which was evident by gel retardation technique. The loading efficiency and loading content were presented (FIG. 16) to support the facts of plasmid pEGFP-N2 loading on nanoparticles.

In an animal study, Balb/C mice (female, 10-12 weeks old, National Laboratory Animal Center, Taipei, Taiwan) were used in the study. Mice were anesthetized using pentobarbital prior to experiment. After removing the hair covering the abdomen, the skin was wiped with an alcohol swab and allowed to air dry. Subsequently, NPs were loaded in an air injector and then bombarded onto the skin. To evaluate expression of the bombarded DNA and the migration of LCs, the mice were sacrificed at specific time. The bombarded skins and skin-draining lymph nodes were collected then examined using CLSM.

In the animal study, nanoparticles loaded with pEGFP-N2 bombarded with an air injector successfully penetrated the skin and EGFP was expressed after 18 hours. The LCs in the lymph nodes was stimulated after bombarded and then migrated to skin-draining lymph nodes after 6 hours. Furthermore, both the nanoparticles and EGFP could be found in the lymph nodes after 18 hours. The results revealed the gCS-coated nanoparticles as a DNA carrier for transdermal DNA delivery via an air injector have the characteristics for tracking skin LCs migration. In one embodiment, the nanoparticles of the present invention also comprise those loaded with any nucleic acids, such as RNA, genes, siRNA, and the like.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A pharmaceutical composition of nanoparticles encapsulating a therapeutically effective amount of at least on bioactive agent, each nanoparticle comprising: a first component of a positively charged chitosan, a second component of a negatively charged substrate that complexes with said first component, at least one quantum dot in a core portion of said nanoparticles, and said at least one bioactive agent, wherein said bioactive agent is encapsulated within said nanoparticles, said nanoparticles having a mean particle size between about 50 and 500 nanometers.

2. The pharmaceutical composition according to claim 1, wherein the nanoparticles from the pharmaceutical composition are freeze-dried, thus producing freeze-dried nanoparticle powders.

3. The pharmaceutical composition according to claim 1, wherein said second component is selected from the group consisting of γ-PGA, α-PGA, soluble salts of PGA, and metal salts of PGA.

4. The pharmaceutical composition according to claim 3, wherein said bioactive agent comprises insulin or insulin analog.

5. The pharmaceutical composition according to claim 1, wherein said bioactive agent is a nucleic acid.

6. The pharmaceutical composition according to claim 5, wherein the nucleic acid is siRNA or plasmid DNA.

7. The pharmaceutical composition according to claim 1, wherein the chitosan is N-trimethyl chitosan, glycol chitosan (gCS), or chitosan derivatives.

8. The pharmaceutical composition according to claim 5, wherein the nucleic acid is an artificial nucleic acid.

9. The pharmaceutical composition according to claim 1, wherein the quantum dot is a CdSe/ZnS quantum dot.

10. The pharmaceutical composition according to claim 1, wherein said bioactive agent is a nucleic acid.

11. The pharmaceutical composition according to claim 10, wherein the nucleic acid is siRNA.

12. The pharmaceutical composition according to claim 10, wherein the nucleic acid is plasmid DNA.

13. The pharmaceutical composition according to claim 10, wherein the nucleic acid is an artificial nucleic acid.

14. The pharmaceutical composition according to claim 1, further comprising poly(lactic-co-glycolic acid) (PLGA) substrate in a core portion of said nanoparticle, wherein said at least one quantum dot is dispersed within said PLGA substrate.

15. The pharmaceutical composition according to claim 14, wherein said bioactive agent is a nucleic acid.

16. The pharmaceutical composition according to claim 15, wherein the nucleic acid is siRNA.

17. The pharmaceutical composition according to claim 15, wherein the nucleic acid is plasmid DNA.

18. The pharmaceutical composition according to claim 15, wherein the nucleic acid is an artificial nucleic acid.

19. The pharmaceutical composition according to claim 14, wherein the chitosan is glycol chitosan (gCS), N-trimethyl chitosan, or chitosan derivatives.

* * * * *